(12) United States Patent
Zhang et al.

(10) Patent No.: US 12,312,319 B2
(45) Date of Patent: May 27, 2025

(54) ISOXAZOLINE COMPOUNDS, THEIR PREPARATION METHODS AND USE

(71) Applicant: METISA BIOTECHNOLOGY CO., LTD, Nanning (CN)

(72) Inventors: Lixin Zhang, Shenyang (CN); Jing Zhang, Shenyang (CN); Yixing Gao, Shenyang (CN); Zhuo Kang, Shenyang (CN)

(73) Assignee: METISA BIOTECHNOLOGY CO., LTD, Nanning (CN)

( * ) Notice: Subject to any disclaimer, the term of this patent is extended or adjusted under 35 U.S.C. 154(b) by 757 days.

(21) Appl. No.: 17/597,225

(22) PCT Filed: Jun. 30, 2020

(86) PCT No.: PCT/CN2020/099377
§ 371 (c)(1),
(2) Date: Dec. 29, 2021

(87) PCT Pub. No.: WO2021/000865
PCT Pub. Date: Jan. 7, 2021

(65) Prior Publication Data
US 2022/0315570 A1    Oct. 6, 2022

(30) Foreign Application Priority Data

Jul. 1, 2019 (CN) .......................... 201910583893.X

(51) Int. Cl.
| | | |
|---|---|---|
| *C07D 261/04* | (2006.01) | |
| *A01N 43/80* | (2006.01) | |
| *A61K 31/42* | (2006.01) | |
| *A61P 33/14* | (2006.01) | |
| *C07D 413/12* | (2006.01) | |

(52) U.S. Cl.
CPC .......... *C07D 261/04* (2013.01); *A01N 43/80* (2013.01); *A61K 31/42* (2013.01); *A61P 33/14* (2018.01); *C07D 413/12* (2013.01)

(58) Field of Classification Search
CPC ..... C07D 261/04; C07D 413/12; A61P 33/14; A61K 31/42; A01N 43/80
See application file for complete search history.

(56) References Cited

FOREIGN PATENT DOCUMENTS

| | | | |
|---|---|---|---|
| CN | 102639529 | A | 8/2012 |
| CN | 103842346 | A | 6/2014 |
| JP | 2008239611 | A | 10/2018 |
| WO | 2012067235 | A1 | 5/2012 |
| WO | 2017140614 | A1 | 8/2017 |
| WO | 2019224143 | | * 11/2019 |

OTHER PUBLICATIONS

International Search Report and Written Opinion issue in International Application No. PCT/CN2020/099377; mailed Sep. 22, 2020; 18 pgs.

* cited by examiner

*Primary Examiner* — D Margaret M Seaman
(74) *Attorney, Agent, or Firm* — HAUPTMAN HAM, LLP

(57) ABSTRACT

An isoxazoline compound, a preparation method therefor and an application thereof. The compound has a structured as represented by general formula I. Also provided is use of the compound represented by general formula I as an insecticide and acaricide as well as an animal parasite control agent.

(I)

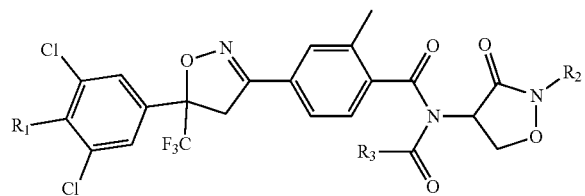

18 Claims, No Drawings

ISOXAZOLINE COMPOUNDS, THEIR PREPARATION METHODS AND USE

CROSS-REFERENCE TO RELATED APPLICATIONS

The present application is a U.S. National Phase of International Application Number PCT/CN2020/099377 filed Jun. 30, 2020, and claims priority to Chinese patent application No. 201910583893.X filed Jul. 1, 2019 before the China Patent Office and entitled "Isoxazoline compound and application thereof".

TECHNICAL FIELD

The invention relates to an isoxazoline compound, and in particular, to a novel isoxazoline compound, preparation method therefor, and application thereof.

BACKGROUND ART

Patent CN102639529A relates to some isoxazoline derivatives with insecticidal activity. However, after applying insecticides and acaricides to pests and mites for a period of time, pests and mites will be resistant to the insecticides and acaricides. So there is a need to continuously develop new and improved compounds with insecticidal and acaricidal activity; at the same time, with increasing demand for agricultural and livestock products and increasing attention to environmental protection, there is always a need to use new insecticides and acaricides with high efficacy, broad-spectrum, and environmental friendliness.

SUMMARY OF THE INVENTION

The invention aims to provide an isoxazoline compound with superior insecticidal and acaricidal activity, preparation method therefor, and application thereof. The isoxazoline compound can be used to prepare drugs for controlling pests and mites in agriculture and other fields, and drugs for controlling animal parasites in the field of veterinary medicine.

In order to achieve the purpose of the invention, the invention provides the technical solutions as follows:

an isoxazoline compound as shown in Formula I:

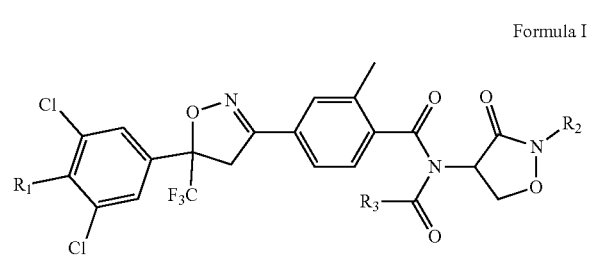

Formula I

In Formula I:
$R_1$ is selected from hydrogen, chlorine, or fluorine;
$R_2$ is selected from ethyl or 2,2,2-trifluoroethyl;
$R_3$ is selected from $C_1$-$C_6$ alkyl, $C_1$-$C_6$ haloalkyl, $C_3$-$C_8$ cycloalkyl, or $C_1$-$C_6$ alkoxy $C_1$-$C_6$ alkyl;
or a stereoisomer of the compound of Formula I;
or a salt of the compound of Formula I;
or a salt of a stereoisomer of the compound of Formula I.

In one possible embodiment, in Formula I,
$R_1$ is selected from hydrogen, chlorine, or fluorine;
$R_2$ is selected from ethyl or 2,2,2-trifluoroethyl;
$R_3$ is selected from $C_1$-$C_4$ alkyl, $C_1$-$C_4$ haloalkyl, $C_3$-$C_4$ cycloalkyl, or $C_1$-$C_4$ alkoxy $C_1$-$C_3$ alkyl.

In one possible embodiment, in Formula I,
$R_1$ is selected from hydrogen, chlorine, or fluorine;
$R_2$ is selected from ethyl or 2,2,2-trifluoroethyl;
$R_3$ is selected from $C_1$-$C_4$ alkyl, cyclopropyl, or $C_1$-$C_4$ alkoxy $C_1$-$C_2$ alkyl.

In one possible embodiment, the salt of the compound of Formula I includes a salt formed by the reaction of the compound of Formula I with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid.

In one possible embodiment, the salt of the stereoisomer of the compound of Formula I includes a salt formed by the reaction of a stereoisomer of the compound of Formula I with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid.

In one possible embodiment, the isoxazoline compound is selected from the compounds in Table 1, which have the structure of Formula I with $R_1$, $R_2$, and $R_3$ being those listed in Table 1:

TABLE 1

| Compound No. | $R_1$ | $R_2$ | $R_3$ |
|---|---|---|---|
| 1 | H | ethyl | methyl |
| 2 | H | ethyl | ethyl |
| 3 | H | ethyl | n-propyl |
| 4 | H | ethyl | isopropyl |
| 5 | H | ethyl | n-butyl |
| 6 | H | ethyl | isobutyl |
| 7 | H | ethyl | tert-butyl |
| 8 | H | ethyl | cyclopropyl |
| 9 | H | ethyl | $CH_3OCH_2$— |
| 10 | H | ethyl | $CH_3CH_2OCH_2$— |
| 11 | H | ethyl | $CH_3CH_2CH_2OCH_2$— |
| 12 | H | ethyl | $(CH_3)_2CHOCH_2$— |
| 13 | H | ethyl | $CH_3CH_2CH_2CH_2OCH_2$— |
| 14 | H | ethyl | $(CH_3)_3COCH_2$— |
| 15 | H | ethyl | $CH_3OCH_2CH_2$— |
| 16 | H | ethyl | $CH_3CH_2OCH_2CH_2$— |
| 17 | H | ethyl | $CH_3CH_2CH_2OCH_2CH_2$— |
| 18 | H | ethyl | $CH_3CH_2CH_2CH_2OCH_2CH_2$— |
| 19 | F | ethyl | methyl |
| 20 | F | ethyl | ethyl |
| 21 | F | ethyl | n-propyl |
| 22 | F | ethyl | isopropyl |
| 23 | F | ethyl | n-butyl |
| 24 | F | ethyl | isobutyl |
| 25 | F | ethyl | tert-butyl |
| 26 | F | ethyl | cyclopropyl |
| 27 | F | ethyl | $CH_3OCH_2$— |
| 28 | F | ethyl | $CH_3CH_2OCH_2$— |
| 29 | F | ethyl | $CH_3CH_2CH_2OCH_2$— |
| 30 | F | ethyl | $(CH_3)_2CHOCH_2$— |
| 31 | F | ethyl | $CH_3CH_2CH_2CH_2OCH_2$— |
| 32 | F | ethyl | $(CH_3)_3COCH_2$— |
| 33 | F | ethyl | $CH_3OCH_2CH_2$— |
| 34 | F | ethyl | $CH_3CH_2OCH_2CH_2$— |
| 35 | F | ethyl | $CH_3CH_2CH_2OCH_2CH_2$— |
| 36 | F | ethyl | $CH_3CH_2CH_2CH_2OCH_2CH_2$— |
| 37 | H | 2,2,2-trifluoroethyl | methyl |

TABLE 1-continued

| Compound No. | $R_1$ | $R_2$ | $R_3$ |
|---|---|---|---|
| 38 | H | 2,2,2-trifluoroethyl | ethyl |
| 39 | H | 2,2,2-trifluoroethyl | n-propyl |
| 40 | H | 2,2,2-trifluoroethyl | isopropyl |
| 41 | H | 2,2,2-trifluoroethyl | n-butyl |
| 42 | H | 2,2,2-trifluoroethyl | isobutyl |
| 43 | H | 2,2,2-trifluoroethyl | tert-butyl |
| 44 | H | 2,2,2-trifluoroethyl | cyclopropyl |
| 45 | H | 2,2,2-trifluoroethyl | $CH_3OCH_2-$ |
| 46 | H | 2,2,2-trifluoroethyl | $CH_3CH_2OCH_2-$ |
| 47 | H | 2,2,2-trifluoroethyl | $CH_3CH_2CH_2OCH_2-$ |
| 48 | H | 2,2,2-trifluoroethyl | $(CH_3)_2CHOCH_2-$ |
| 49 | H | 2,2,2-trifluoroethyl | $CH_3CH_2CH_2CH_2OCH_2-$ |
| 50 | H | 2,2,2-trifluoroethyl | $(CH_3)_3COCH_2-$ |
| 51 | H | 2,2,2-trifluoroethyl | $CH_3OCH_2CH_2-$ |
| 52 | H | 2,2,2-trifluoroethyl | $CH_3CH_2OCH_2CH_2-$ |
| 53 | H | 2,2,2-trifluoroethyl | $CH_3CH_2CH_2OCH_2CH_2-$ |
| 54 | H | 2,2,2-trifluoroethyl | $CH_3CH_2CH_2CH_2OCH_2CH_2-$ |
| 55 | F | 2,2,2-trifluoroethyl | methyl |
| 56 | F | 2,2,2-trifluoroethyl | ethyl |
| 57 | F | 2,2,2-trifluoroethyl | n-propyl |
| 58 | F | 2,2,2-trifluoroethyl | isopropyl |
| 59 | F | 2,2,2-trifluoroethyl | n-butyl |
| 60 | F | 2,2,2-trifluoroethyl | isobutyl |
| 61 | F | 2,2,2-trifluoroethyl | tert-butyl |
| 62 | F | 2,2,2-trifluoroethyl | cyclopropyl |
| 63 | F | 2,2,2-trifluoroethyl | $CH_3OCH_2-$ |
| 64 | F | 2,2,2-trifluoroethyl | $CH_3CH_2OCH_2-$ |
| 65 | F | 2,2,2-trifluoroethyl | $CH_3CH_2CH_2OCH_2-$ |
| 66 | F | 2,2,2-trifluoroethyl | $(CH_3)_2CHOCH_2-$ |
| 67 | F | 2,2,2-trifluoroethyl | $CH_3CH_2CH_2CH_2OCH_2-$ |
| 68 | F | 2,2,2-trifluoroethyl | $(CH_3)_3COCH_2-$ |
| 69 | F | 2,2,2-trifluoroethyl | $CH_3OCH_2CH_2-$ |
| 70 | F | 2,2,2-trifluoroethyl | $CH_3CH_2OCH_2CH_2-$ |
| 71 | F | 2,2,2-trifluoroethyl | $CH_3CH_2CH_2OCH_2CH_2-$ |
| 72 | F | 2,2,2-trifluoroethyl | $CH_3CH_2CH_2CH_2OCH_2CH_2-$ |
| 73 | Cl | ethyl | methyl |
| 74 | Cl | ethyl | ethyl |
| 75 | Cl | ethyl | n-propyl |
| 76 | Cl | ethyl | isopropyl |
| 77 | Cl | ethyl | n-butyl |
| 78 | Cl | ethyl | isobutyl |
| 79 | Cl | ethyl | tert-butyl |
| 80 | Cl | ethyl | cyclopropyl |
| 81 | Cl | ethyl | $CH_3OCH_2-$ |
| 82 | Cl | ethyl | $CH_3CH_2OCH_2-$ |
| 83 | Cl | ethyl | $CH_3CH_2CH_2OCH_2-$ |
| 84 | Cl | ethyl | $(CH_3)_2CHOCH_2-$ |
| 85 | Cl | ethyl | $CH_3CH_2CH_2CH_2OCH_2-$ |
| 86 | Cl | ethyl | $(CH_3)_3COCH_2-$ |
| 87 | Cl | ethyl | $CH_3OCH_2CH_2-$ |
| 88 | Cl | ethyl | $CH_3CH_2OCH_2CH_2-$ |
| 89 | Cl | ethyl | $CH_3CH_2CH_2OCH_2CH_2-$ |
| 90 | Cl | ethyl | $CH_3CH_2CH_2CH_2OCH_2CH_2-$ |
| 91 | Cl | 2,2,2-trifluoroethyl | methyl |
| 92 | Cl | 2,2,2-trifluoroethyl | ethyl |
| 93 | Cl | 2,2,2-trifluoroethyl | n-propyl |
| 94 | Cl | 2,2,2-trifluoroethyl | isopropyl |
| 95 | Cl | 2,2,2-trifluoroethyl | n-butyl |
| 96 | Cl | 2,2,2-trifluoroethyl | isobutyl |
| 97 | Cl | 2,2,2-trifluoroethyl | tert-butyl |
| 98 | Cl | 2,2,2-trifluoroethyl | cyclopropyl |
| 99 | Cl | 2,2,2-trifluoroethyl | $CH_3OCH_2-$ |
| 100 | Cl | 2,2,2-trifluoroethyl | $CH_3CH_2OCH_2-$ |
| 101 | Cl | 2,2,2-trifluoroethyl | $CH_3CH_2CH_2OCH_2-$ |
| 102 | Cl | 2,2,2-trifluoroethyl | $(CH_3)_2CHOCH_2-$ |
| 103 | Cl | 2,2,2-trifluoroethyl | $CH_3CH_2CH_2CH_2OCH_2-$ |
| 104 | Cl | 2,2,2-trifluoroethyl | $(CH_3)_3COCH_2-$ |
| 105 | Cl | 2,2,2-trifluoroethyl | $CH_3OCH_2CH_2-$ |
| 106 | Cl | 2,2,2-trifluoroethyl | $CH_3CH_2OCH_2CH_2-$ |
| 107 | Cl | 2,2,2-trifluoroethyl | $CH_3CH_2CH_2OCH_2CH_2-$ |
| 108 | Cl | 2,2,2-trifluoroethyl | $CH_3CH_2CH_2CH_2OCH_2CH_2-$ | or a stereoisomer of any one of the compounds from Table 1;

or a salt formed by the reaction of any one of the compounds from Table 1 with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid;

or a salt formed by the reaction of a stereoisomer of any one of the compounds from Table 1 with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid.

In one possible embodiment, the isoxazoline compound is selected from the compounds in Table 2, which have the structure of Formula I with $R_1$, $R_2$, and $R_3$ being those listed in Table 2:

TABLE 2

| Compound No. | $R_1$ | $R_2$ | $R_3$ |
|---|---|---|---|
| 1 | H | ethyl | methyl |
| 2 | H | ethyl | ethyl |
| 3 | H | ethyl | n-propyl |
| 4 | H | ethyl | isopropyl |
| 5 | H | ethyl | n-butyl |
| 6 | H | ethyl | isobutyl |
| 7 | H | ethyl | tert-butyl |
| 8 | H | ethyl | cyclopropyl |
| 9 | H | ethyl | $CH_3OCH_2-$ |
| 10 | H | ethyl | $CH_3CH_2OCH_2-$ |
| 11 | H | ethyl | $CH_3CH_2CH_2OCH_2-$ |
| 12 | H | ethyl | $(CH_3)_2CHOCH_2-$ |
| 19 | F | ethyl | methyl |
| 20 | F | ethyl | ethyl |
| 21 | F | ethyl | n-propyl |
| 22 | F | ethyl | isopropyl |
| 23 | F | ethyl | n-butyl |
| 24 | F | ethyl | isobutyl |
| 25 | F | ethyl | tert-butyl |
| 26 | F | ethyl | cyclopropyl |
| 27 | F | ethyl | $CH_3OCH_2-$ |
| 28 | F | ethyl | $CH_3CH_2OCH_2-$ |
| 29 | F | ethyl | $CH_3CH_2CH_2OCH_2-$ |
| 30 | F | ethyl | $(CH_3)_2CHOCH_2-$ |
| 37 | H | 2,2,2-trifluoroethyl | methyl |
| 38 | H | 2,2,2-trifluoroethyl | ethyl |
| 39 | H | 2,2,2-trifluoroethyl | n-propyl |
| 40 | H | 2,2,2-trifluoroethyl | isopropyl |
| 41 | H | 2,2,2-trifluoroethyl | n-butyl |
| 42 | H | 2,2,2-trifluoroethyl | isobutyl |
| 43 | H | 2,2,2-trifluoroethyl | tert-butyl |
| 44 | H | 2,2,2-trifluoroethyl | cyclopropyl |
| 45 | H | 2,2,2-trifluoroethyl | $CH_3OCH_2-$ |
| 46 | H | 2,2,2-trifluoroethyl | $CH_3CH_2OCH_2-$ |
| 47 | H | 2,2,2-trifluoroethyl | $CH_3CH_2CH_2OCH_2-$ |
| 48 | H | 2,2,2-trifluoroethyl | $(CH_3)_2CHOCH_2-$ |
| 55 | F | 2,2,2-trifluoroethyl | methyl |
| 56 | F | 2,2,2-trifluoroethyl | ethyl |
| 57 | F | 2,2,2-trifluoroethyl | n-propyl |
| 58 | F | 2,2,2-trifluoroethyl | isopropyl |
| 59 | F | 2,2,2-trifluoroethyl | n-butyl |
| 60 | F | 2,2,2-trifluoroethyl | isobutyl |
| 61 | F | 2,2,2-trifluoroethyl | tert-butyl |
| 62 | F | 2,2,2-trifluoroethyl | cyclopropyl |
| 63 | F | 2,2,2-trifluoroethyl | $CH_3OCH_2-$ |
| 64 | F | 2,2,2-trifluoroethyl | $CH_3CH_2OCH_2-$ |
| 65 | F | 2,2,2-trifluoroethyl | $CH_3CH_2CH_2OCH_2-$ |
| 66 | F | 2,2,2-trifluoroethyl | $(CH_3)_2CHOCH_2-$ |
| 73 | Cl | ethyl | methyl |
| 74 | Cl | ethyl | ethyl |
| 75 | Cl | ethyl | n-propyl |
| 76 | Cl | ethyl | isopropyl |
| 77 | Cl | ethyl | n-butyl |

TABLE 2-continued

| Compound No. | $R_1$ | $R_2$ | $R_3$ |
|---|---|---|---|
| 78 | Cl | ethyl | isobutyl |
| 79 | Cl | ethyl | tert-butyl |
| 80 | Cl | ethyl | cyclopropyl |
| 81 | Cl | ethyl | $CH_3OCH_2$— |
| 82 | Cl | ethyl | $CH_3CH_2OCH_2$— |
| 83 | Cl | ethyl | $CH_3CH_2CH_2OCH_2$— |
| 84 | Cl | ethyl | $(CH_3)_2CHOCH_2$— |
| 91 | Cl | 2,2,2-trifluoroethyl | methyl |
| 92 | Cl | 2,2,2-trifluoroethyl | ethyl |
| 93 | Cl | 2,2,2-trifluoroethyl | n-propyl |
| 94 | Cl | 2,2,2-trifluoroethyl | isopropyl |
| 95 | Cl | 2,2,2-trifluoroethyl | n-butyl |
| 96 | Cl | 2,2,2-trifluoroethyl | isobutyl |
| 97 | Cl | 2,2,2-trifluoroethyl | tert-butyl |
| 98 | Cl | 2,2,2-trifluoroethyl | cyclopropyl |
| 99 | Cl | 2,2,2-trifluoroethyl | $CH_3OCH_2$— |
| 100 | Cl | 2,2,2-trifluoroethyl | $CH_3CH_2OCH_2$— |
| 101 | Cl | 2,2,2-trifluoroethyl | $CH_3CH_2CH_2OCH_2$— |
| 102 | Cl | 2,2,2-trifluoroethyl | $(CH_3)_2CHOCH_2$— | or a stereoisomer of any one of the compounds from Table 2;

or a salt formed by the reaction of any one of the compounds from Table 2 with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid;

or a salt formed by the reaction of a stereoisomer of any one of the compounds from Table 2 with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid.

In the compound of Formula I of the present invention, the compound of Formula I has two chiral carbon atoms (i.e. the carbon atoms labeled with * and **, respectively, in the following Formula I), and consequently, four stereoisomers can be produced as a result of the chiral centers represented by *C and **C atoms in the compound of Formula Is: the compound of the Formula I-1 (both *C and **C are in S configuration), the compound of the Formula I-2 (*C is in S configuration, **C is in R configuration), the compound of the Formula I-3 (*C is in R configuration, **C is in S configuration), and the compound of the Formula I-4 (both *C and **C are in R configuration).

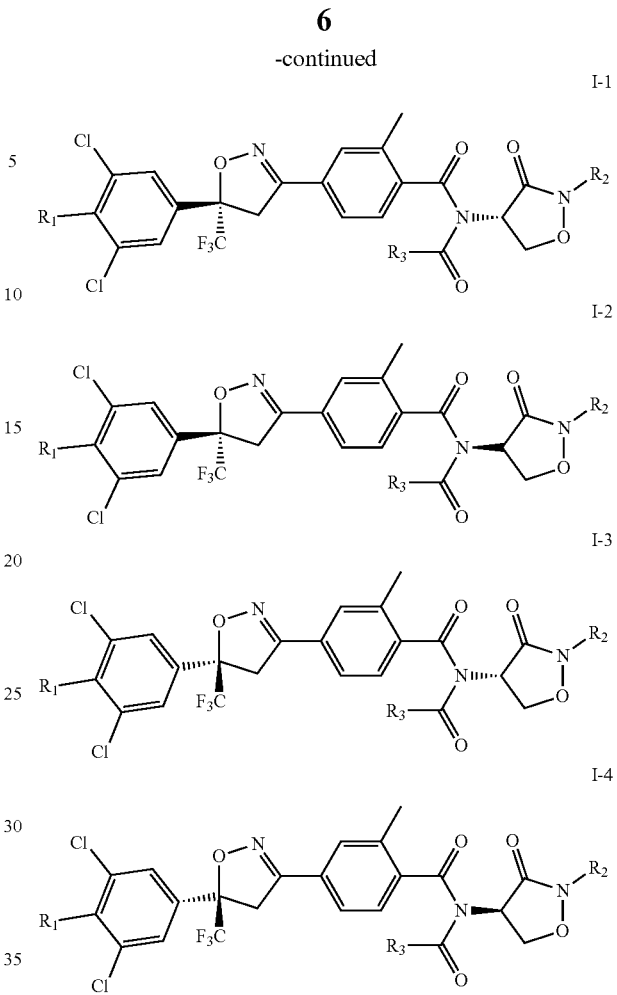

The invention also includes any one of the compounds of Formula I-1, Formula I-2, Formula I-3, and Formula I-4, and a mixture thereof in all possible forms.

When the compound of Formula I-2 and the compound of Formula I-4 are mixed in a molar ratio of approximately 1:1, it can be expressed by Formula IA (*C exists as a racemate, **C is in R configuration); When the compound of Formula I-1 and the compound of Formula I-3 are mixed in a molar ratio of approximately 1:1, it can be expressed by Formula IB (*C exists as a racemate, **C is in S configuration); When the compound of the Formula I-1 and the compound of the Formula I-2 are mixed in a molar ratio of approximately 1:1, it can be represented by the Formula IC (*C is in S configuration, **C exists as a racemate); When the compound of Formula I-3 and the compound of Formula I-4 are mixed in a molar ratio of approximately 1:1, it can be represented by Formula ID (*C is in R configuration and **C exists as a racemate).

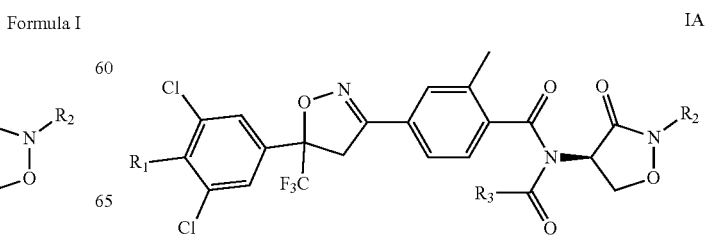

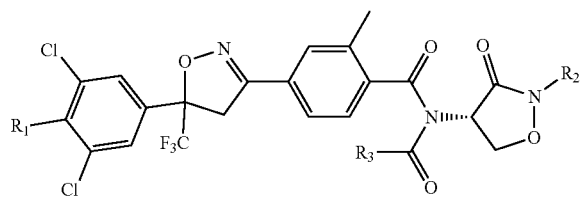

IB

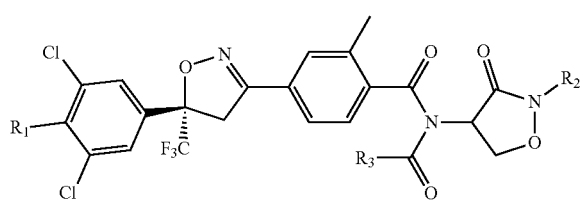

IC

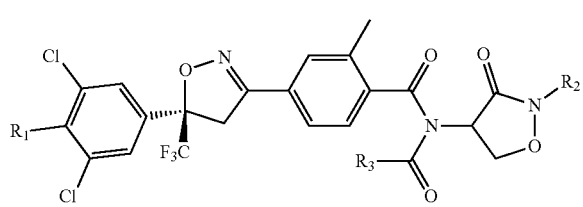

ID

In addition, one stereoisomer of the compound of Formula I of the present invention can be mixed with another stereoisomer thereof in any molar ratio, for example, in a molar ratio of 1:99 to 99:1, or in a molar ratio of 10:1 to 1:10.

In one possible embodiment, the stereoisomer of the compound of Formula I is the compound as shown in Formula IA.

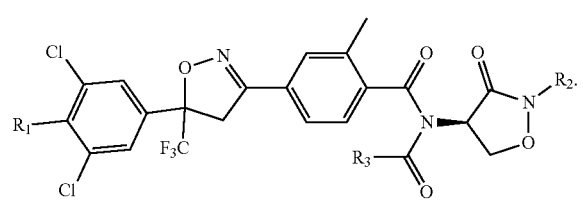

Formula IA

In one possible embodiment, the compound as shown in Formula IA is selected from the compounds in Table 3, which have the structure of Formula IA with $R_1$, $R_2$, and $R_3$ being those listed in Table 3:

TABLE 3

| Compound No. | $R_1$ | $R_2$ | $R_3$ |
|---|---|---|---|
| 109 | H | ethyl | methyl |
| 110 | H | ethyl | ethyl |
| 111 | H | ethyl | isopropyl |
| 112 | H | ethyl | cyclopropyl |
| 113 | H | ethyl | $CH_3OCH_2$— |
| 114 | H | ethyl | $CH_3CH_2OCH_2$— |
| 115 | H | ethyl | $CH_3OCH_2CH_2$— |
| 116 | H | ethyl | $CH_3CH_2OCH_2CH_2$— |
| 117 | F | ethyl | methyl |
| 118 | F | ethyl | ethyl |

TABLE 3-continued

| Compound No. | $R_1$ | $R_2$ | $R_3$ |
|---|---|---|---|
| 119 | F | ethyl | isopropyl |
| 120 | F | ethyl | cyclopropyl |
| 121 | F | ethyl | $CH_3OCH_2$— |
| 122 | F | ethyl | $CH_3CH_2OCH_2$— |
| 123 | F | ethyl | $CH_3OCH_2CH_2$— |
| 124 | F | ethyl | $CH_3CH_2OCH_2CH_2$— |

In one possible embodiment, the compound as shown in Formula IA is selected from the compounds in Table 4, which have the structure of Formula IA with $R_1$, $R_2$, and $R_3$ being those listed in Table 4:

TABLE 4

| Compound No. | $R_1$ | $R_2$ | $R_3$ |
|---|---|---|---|
| 109 | H | ethyl | methyl |
| 110 | H | ethyl | ethyl |
| 111 | H | ethyl | isopropyl |
| 112 | H | ethyl | cyclopropyl |
| 113 | H | ethyl | $CH_3OCH_2$— |
| 114 | H | ethyl | $CH_3CH_2OCH_2$— |
| 117 | F | ethyl | methyl |
| 118 | F | ethyl | ethyl |
| 119 | F | ethyl | isopropyl |
| 120 | F | ethyl | cyclopropyl |
| 121 | F | ethyl | $CH_3OCH_2$— |
| 122 | F | ethyl | $CH_3CH_2OCH_2$— |

In an embodiment, the invention also provides a method for preparing the isoxazoline compound described above, which is as follows:

(1) When the isoxazoline compound is the compound of Formula I, its preparation method is as follows (the definition of each group in the reaction formula is the same as that mentioned above unless otherwise stated):

The compounds of Formula II and Formula III are allowed to react in a solvent at a temperature from −10° C. to the boiling point of the solvent for 0.5-48 hours to prepare the compound of Formula I; the reaction can be carried out in the presence of alkali.

(2) When the isoxazoline compound is a stereoisomer of the compound of Formula I, it can be obtained by conventional methods, for example, obtaining reaction products with corresponding optical activity from reaction raw materials with optical activity, and chiral resolution of racemic or meso reaction products.

(3) When the isoxazoline compound is a salt of the compound of Formula I or a salt of a stereoisomer of the compound of Formula I, its preparation method is as follows: the compound of Formula I or the stereoisomer of the compound of Formula I is used as reaction raw material to form acid addition salts with corresponding acids by a conventional method; for example, a salt of hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid can be prepared.

In one possible embodiment, the solvent include one or more selected from the group consisting of: aromatic hydrocarbons such as benzene, toluene, or xylene, ketones such as acetone, methyl ethyl ketone, or methyl isobutyl ketone, halogenated hydrocarbons such as chloroform or dichloromethane, esters such as methyl acetate or ethyl acetate, ethers such as tetrahydrofuran, dioxane, diethyl ether, or 1,2-dimethoxyethane, polar solvents such as water, acetonitrile, N,N-dimethylformamide, N-methylpyrrolidinone, or dimethylsulfoxide; and alkalis include one or more selected from the group consisting of: organic bases such as triethylamine, pyridine, DBU, or 4-dimethylaminopyridine, alkali metal hydrides such as sodium hydride or potassium hydride, alkali metal hydroxides such as sodium hydroxide or potassium hydroxide, alkaline earth metal hydroxides such as calcium hydroxide, alkali metal carbonates such as sodium carbonate or potassium carbonate, alkali metal bicarbonates such as sodium bicarbonate, and metal alkoxides such as sodium methoxide or potassium ethoxide.

The intermediate compound of Formula II or stereoisomers thereof can be prepared according to well-known methods, for example, according to the method reported in WO2011067272, WO2013050302, WO2014019950, WO2014029640, WO2014029709, or WO2014029639, etc.

The compound of Formula III is usually commercially available, and can also be made by conventional methods.

In an embodiment, the invention also provides use of the isoxazoline compound described above in the preparation of an insecticide and/or acaricide.

In one possible embodiment, the insecticide is used to control one or more of the following insects:

beetles (Coleopteran), such as Callosobruchus *Chinensis, Sitophilus zeamais*, Tribolium Castaneum, *Epilachna vigintioctomaculata, Agriotes* ogurae fuscicollis, *Anomala* rufocuprea, *Leptinotarsa decemlineata, Diabrotica* spp., Monochamus alternatus endai, *Lissorhoptrus oryzophilus*, or *Lyctus bruneus*;

lepidopteran pests, such as *Lymantria dispar, Malacosoma neustria, Pieris rapae* crucivora, *Spodoptera litura, Mamestra brassicae, Chilo suppressalis, Ostrinia nubilalis, Cadra cautella*, chyanokokakumonmaki (*Adoxophyes honmai*), *Cydia pomonella, Agrotis segetum, Galleria mellonella, Plutella xylostella, Helicoverpa armigera*, or *Phylloccinis citrella*; hemipterous pests, such as *Nephotettix cincticeps, Nilaparvata lugens, Pseudococcus comstocki, Unaspis yanonensis, Myzus persicas, Aphis pomi, Aphis gossypii, Lipaphis erysimi, Stephanitis nashi, Nezara* spp., *Trialeurodes vaporariorum*, or Pshylla spp.;

thysanoptera pests, such as *Thrips palmi* or Franklinella *occidentalis*; orthopteran pests, such as *Gryllotalpa Africana* or *Locusta migratoria*; blattarian pests, such as *Blattella germanica, Periplaneta americana, Reticulitermes speratus*, or *Coptotermes formosanus*;

dipterous pests, such as *Musca domestica*, Aedesaegypti, *Delia platura, Culex pipiens pallens, Anopheles sinensis, Culex tritaeniorhynchus, Liriomyza trifolii*, and the like.

In one possible embodiment, the acaricide is used to control one or more of the following mites: *Tetranychus cinnabarinus, Tetrahychus urticae, Panonychus citri*, Aculops pelekassi, Tarsonemus spp., and the like.

In one possible embodiment, the insecticide and/or acaricide is used to control one or more of *Leucania separata, Plutella xylostella, Chilo suppressalis*, and *Tetranychus cinnabarinus*.

In an embodiment, the invention also provides an insecticide formulation or acaricide formulation, which comprises the above isoxazoline compound as an active ingredient and one or more adjuvants.

In one possible embodiment, the insecticide formulation or acaricide formulation is in a dosage form selected from the group consisting of: a solution, an emulsion, a wettable powder, a granular wettable powder, a suspending agent, a powder, a foaming agent, an ointment, a tablet, a granule, an aerosol, a natural agent impregnated with active compounds, a synthetic agent impregnated with active compounds, a microcapsule, a seed coating agent, a preparation equipped with a combustion device (the combustion device may be a flue stack, a spray barrel, a tank, or a coiled pipe, etc.), ULV (a cold fogging concentrate, a hot fogging concentrate), etc. These insecticide formulations or acaricide formulations or animal parasite control agents can be prepared by known methods, for example, by mixing an active ingredient with a filler (for example, a liquid diluent or carrier, a liquefied gas diluent or carrier, a solid diluents or carrier), and optionally a surfactant (i.e., an emulsifier and/or dispersant and/or foaming agent), and the like.

In one possible embodiment, the adjuvant may include one or more of the followings: a filler (such as a liquid diluent or carrier, a liquefied gas diluent or carrier, a solid diluent or carrier), a surfactant (such as an emulsifier and/or dispersant and/or foaming agent), an adhesive, and a coloring agent;

Liquid diluents or carriers may include, for example, aromatic hydrocarbons (xylene, toluene, alkyl naphthalene, etc.), chlorinated aromatic hydrocarbons or chlorinated aliphatic hydrocarbons (e.g., chlorobenzene, vinyl chloride, dichloromethane, etc.), aliphatic hydrocarbons (e.g., cyclohexane or paraffin wax (e.g., mineral oil fractions)), alcohols (e.g., butanol, ethylene glycol, and ethers or esters thereof, etc.), and ketones (e.g., acetone, methyl ethyl ketone, methyl isobutyl ketone, cyclohexanone, etc.), strong polar solvents (e.g., dimethylformamide, dimethylsulfoxide), water, etc. When water is used as a filler, for example, an organic solvent can be used as a cosolvent;

Liquefied gas diluents or carriers may include those existing in the form of gas at atmospheric pressure and temperature, for example, propane, nitrogen, carbon dioxide, as well as aerosol propellants such as halogenated hydrocarbon; Solid diluents may include crushed natural minerals (such as kaolin, clay, talc, chalk, quartz, attapulgite, montmorillonite, or diatomite, etc.) and crushed synthetic minerals (such as finely dispersed silicic acid, alumina, and silicate, etc.), and the like; Emulsifiers and/or foaming agents may include nonionic and anionic emulsifiers (for example, polyoxyethylene fatty acid esters, polyoxyethylene fatty acid alcohol ethers (such as alkyl aryl polyethylene glycol ethers), alkyl sulfonates, alkyl sulfates, and aryl sulfonates) and albumin hydrolysates, and the like;

Dispersants may include lignin sulfite liquid waste and methyl cellulose; Adhesives may include carboxymethyl cellulose, natural or synthetic polymers (for example, acacia, polyvinyl, alcohol, polyvinyl acetate, etc.).

Coloring agents may include inorganic pigments (for example, iron oxide, titanium oxide, Prussian blue, etc.), organic dyes such as alizarin dyes, azo dyes, or metal phthalocyanine dyes; and trace elements such as iron salts, manganese salts, boron salts, copper salts, cobalt salts, molybdenum salts, or zinc salts.

In addition, the isoxazoline compound of the present invention may exist as a mixture with a synergist which does not need to have activity by itself. More specifically, it is a compound that enhances the activity of active compounds.

In one possible embodiment, the amount of the above-mentioned isoxazoline compound contained in the insecticide formulation or acaricide formulation is 0.1 to 99% by weight, optionally 0.5 to 90% by weight.

In an embodiment, the present invention also provides an insecticide composition or acaricide composition, which comprises a mixture of the above-mentioned isoxazoline compound and additional active compound(s) (for example, an insecticide, a poison bait, a disinfectant, an acaricide, a nematicide, a fungicide, a growth regulator, an herbicide, etc.). The mixture can be provided in the form of bulk drug, or in the form of commercially available formulation, or in the usage form made from its formulation.

In an embodiment, the present invention also provides a method for controlling agricultural or forestry pests and/or mites, which comprises the following steps: applying an effective dose of material to the pests and/or mites to be controlled, or to their growth media, wherein the material is one or more selected from the group consisting of: the isoxazoline compound, the insecticide formulation or acaricide formulation, the insecticide composition or acaricide composition described above.

In an embodiment, the invention also provides use of the isoxazoline compound in the preparation of animal parasite control agents. In the field of veterinary medicine, namely, veterinary science, the isoxazoline compound of the present invention may be effective for combating various harmful animal parasites, especially internal parasites and external parasites.

In one possible embodiment, the animal parasites include one or more of the followings: Anoplurida, such as *Haematopinus* spp., *Linognathus* spp., *Pediculus* spp., *Phtirus* spp., and *Solenopots* spp.; particularly, the representative examples are *Linognathus setosus* and *Solenopotes capillartus*; Mallophaga (*Linognathus vituli*, *Linognathus ovillus*, *Linognathus oviformis*, *Linognathus pedalis*, *Linognathus stenopsis*, *Haematopinus asini macrocephalus*, *Haematopinus eurysternus*, *Haematopinus suis*, *Pediculus humanus capitis*, *Pediculus humanus corporis*, *Phylloera vastatrix*, *Phthirus pubis*), Amblycerina and Ischnocerin, such as *Trimenopon* spp., *Menopon* spp., *Trinoton* spp., *Bovicola* spp., *Werneckiella* spp., *Lepikentron* spp., *Damalina* spp., *Trichodectes* spp, and *Felicola* spp.; particularly, the representative examples are *Bovicola bovis*, *Bovicola ovis*, *Bovicola limbata*, *Damalina bovis*, *Trichodectes canis*, *Felicola subrostratus*, *Bovicola caprae*, *Lepikentron ovis*, *Werneckiella equi*, etc.; Diptera, Nematocerina and Brachycerina, such as *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particularly, the representative examples are *Aedes aegypti*, *Aedes albopictus*, *Aedes taeniorhynchus*, *Anopheles gambiae*, *Anopheles maculipennis*, *Calliphora erythrocephala*, *Chrysozona pluvialis*, *Culex quinquefasciatus*, *Culex pipiens*, *Culex tarsalis*, *Fannia canicularis*, *Sarcophaga carnaria*, *Stomoxys calcitrans*, *Tipula paludosa*, *Lucilia cuprina*, *Lucilia sericata*, *Simulium reptans*, *Phlebotomus papatasi*, *Phlebotomus longipalpis*, *Odagmia ornata*, *Wilhelmia equina*, *Boophthora erythrocephala*, *Tabanus bromius*, *Tabanus spodopterus*, *Tabanus atratus*, *Tabanus sudeticus*, *Hybomitra ciurea*, *Chrysops caecutiens*, *Chrysops relictus*, *Haematopota pluvialis*, *Haematopota Italica*, *Musca autumnalis*, *Musca domestica*, *Haematobia irritans irritans*, *Haematobia irritans exigua*, *Haematobia stimulans*, *Hydrotaea irritans*, *Hydrotaea albipuncta*, *Chrysomya chloropyga*, *Chrysomya bezziana*, *Oestrus ovis*, *Hypoderma bovis*, *Hypoderma lineatum*, *Przhevalskiana silenus*, *Dermatobia hominis*, *Melophagus ovinus*, *Lipoptena capreoli*, *Lipoptena cervi*, *Hippobosca variegata*, *Hippobosca equina*, *Gasterophilus intestinalis*, *Gasterophilus haemorrhoidalis*, *Gasterophilus interrnis*, *Gasterophilus nasalis*, *Gasterophilus nigricornis*, *Gasterophilus pecorum*, *Braula coeca*; Siphonapterida, such as *Pulex* spp., *Ctenocephalides* spp., *Tunga* spp., *Xenopsylla* spp., *Ceratophyllus* spp., particularly, the representative examples are *Ctenocephalides canis*, *Ctenocephalides felis*, *Pulex irritans*, *Tunga penetrans*, *Xenopsylla cheopis*; Heteropterida, such as *Cimex* spp., *Triatoma* spp., *Rhodnius* spp., *Panstrongylus* spp.; Blattarida, such as *Blatta orientalis*, *Periplaneta americana*, *Blatta germanica*, *Supella* spp., *Suppella longipalpa*; Acari (*Acarina*), Metastigmata and Mesostigmata, such as *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp. (original species of heteroecious mites), *Ornithonyssus* spp., *Pneumonyssus* spp., *Pneumonyssus* spp., *Raillietia* spp., *Pneumonyssus* spp., *Sternostoma* spp., *Varroa* spp., *Acarapis* spp.; particularly, the representative examples are *Argas persicus*, *Argas reflexus*, *Ornithodorus moubata*, *Otobius megnini*, *Rhipicephalus* (*Boophilus*) *microplus*, *Rhipicephalus* (*Boophilus*) *decoloratus*, (*Rhipicephalus* (*Boophilus*) *annulatus*), *Rhipicephalus*(*Boophilus*)calceratus, *Hyalomma anatolicum*, Hyalommaaegypticum, *Hyalomma marginatum*, *Hyalomma transiens*, Rhipicephalusevertsi, *Ixodes ricinus*, *Ixodes hexagonus*, *Ixodes canisuga*, *Ixodes pilosus*, *Ixodes rubicundus*, *Ixodes scapularis*, *Ixodes holocyclus*, *Haemaphysalis concinna*, *Haemaphysalis punctata*, *Haemaphysalis cinnabarina*, *Haemaphysalis otophila*, *Haemaphysalis leachi*, *Haemaphysalis longicorni*, *Dermacentor marginatus*, *Dermacentor reticulatus*, *Dermacentor pictus*, *Dermacentor albipictus*, *Dermacentor andersoni*, *Dermacentor variabilis*, *Hyalomma mauritanicum*, *Rhipicephalus sanguineus*, *Rhipicephalus bursa*, *Rhipicephalus appendiculatus*, *Rhipicephalus capensis*, *Rhipicephalus turanicus*, *Rhipicephalus zambeziensis*, *Amblyomma americanum*, *Amblyomma variegatum*, *Amblyomma maculatum*, *Amblyo-

*mma hebraeum, Amblyomma cajennense, Dermanyssus gallinae, Ornithonyssus bursa, Ornithonyssus sylviarum, Varroa* jacobsconi; Actinedida (Prostigmata) and Acaridida (*Astigmata*), such as *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; particularly, *C. heyletiella yasguri, C. heyletiella blakei, Demodex canis, Demodex bovis, Demodex ovis, Demodex caprae, Demodex equi, Demodex caballi, Demodex suis, Neotrombicula autumnalis, Neotrombiculadesaleli, Neoschonegastia xerothermobia, Trombicula akamushi, Otodectes cynotis, Notoedres cati, Sarcoptis canis, Sarcoptes bovis, Sarcoptes ovis, Sarcoptes rupicaprae (S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi*; Nematodes, such as *Meloidogyne incognita, Bursaphelenchus xylophilus, Aphelenchoides besseyi, Heterodera glycines, Pratylenchus* spp., and the like; Arthropods, worms, and plasmodia that invade animals. Controlling arthropods, worms, and/or plasmodia can reduce the mortality of domestic animals and improve the productivity (meat, milk, hair, skin, eggs, and honey) and health of animals.

In one possible embodiment, the animal parasite control agent is used to control one or more of cat fleas and American dog ticks.

In one possible embodiment, the animal includes one or more of the followings: agricultural animals, such as cattles, sheeps, goats, horses, pigs, donkeys, camels, buffaloes, rabbits, chickens, turkeys, ducks, geese, farmed fishes, bees, etc.; further include pets called companion animals, such as dogs, cats, caged birds, aquarium fish; and also include experimental animals, such as hamsters, guinea-pig, rats, mice, etc.

In an embodiment, the invention also provides an animal parasite control agent, which contains the isoxazoline compound described above as an active ingredient and one or more adjuvants.

In one possible embodiment, the animal parasite control agent is in a dosage form selected from the group consisting of: a tablet, a capsule, a drink, a drinkable drug, a granule, an ointment, and a pill, a suppository, an injection (intramuscularly, subcutaneously, intravenously, intraperitoneally, etc.), a smear, an aerosol, a pressureless spray (such as a pump spray and aerosol spray).

In one possible embodiment, the amount of the active ingredient contained in the animal parasite control agent is 1 to 80 wt %.

In an embodiment, the present invention also provides an animal parasite control composition, which comprises a mixture of the isoxazoline compound mentioned above and other animal parasite control active compounds (such as an acaricide, an insecticide, a parasiticide, an antiplasmodium agent, etc.). The mixture can be provided in the form of bulk drug, or in the form of commercially available formulation, or in the usage form made from its formulation.

In an embodiment, the invention also provides a method for controlling animal parasites, which comprises the following steps: applying an effective dose of material to the animal parasites to be controlled, or to their growth media, wherein the material is one or more selected from the group consisting of: the isoxazoline compound, the animal parasite control agent, and the animal parasite control composition described above. For example, enteral administration can be carried out by employing tablets, capsules, drinks, drinkable drugs, granules, ointments, pills, or suppositories; parenteral administration based on skin administration such as injection (intramuscularly, subcutaneously, intravenously, intraperitoneally, etc.), implantation, nasal administration, may include bathing or soaking, spraying, pouring, dropping, cleaning, or dusting, and can be carried out by using molding products (such as a collars, an ear tag, a label, a leg brace, a net, a marker, etc.) containing active compounds. The active compounds of the invention have low toxicity, and thus can be safely applied to warm-blooded animals.

Beneficial Effects

The isoxazoline compounds of the present invention have unexpectedly excellent insecticidal and acaricidal efficacies, and also exhibit appropriate control efficacy on poisonous pests without phytotoxicity to cultivated crops and plants. In addition, the compounds of the present invention may be used to control, disinfect, and kill various pests, such as harmful piercing-sucking insects, chewing insects, and other plant parasitic pests, stored grain pests, sanitary pests, and the like.

DETAILED DESCRIPTION OF THE INVENTION

In order to make the purpose, technical solutions and advantages of the embodiments of the invention clearer, the technical solutions in the embodiments of the invention will be described clearly and completely, obviously, the described embodiments are some of the embodiments of the present invention, but not all of them. Based on the embodiments of the present invention, all other embodiments obtained by those of ordinary skill in the art without creative work are within the scope of the present invention.

In addition, in order to better explain the present invention, a lot of specific details are given in the following embodiments. It will be understood by those skilled in the art that the present invention may be practiced without certain specific details. In some embodiments, materials, elements, methods, means, etc., well known to those skilled in the art, are not described in detail so as to highlight the spirit of the present invention.

Throughout the specification and claims, the term "comprising" or variations thereof, such as "including" or "containing" and the like, will be understood to include the stated components and not to exclude other elements or other components, unless expressly indicated otherwise.

Unless otherwise indicated, all raw materials used are commercially available.

In the present invention, the terms used have the following meanings:

In the definitions of compounds of the general formulae given above, the collective terms used generally represent the following substituents:

Alkyl: linear or branched alkyl, such as methyl, ethyl, n-propyl, isopropyl, or various butyl, pentyl, or hexyl isomers.

Haloalkyl: linear or branched alkyl, in which part or all of hydrogen atoms can be substituted with halogen atoms, such as chloromethyl, dichloromethyl, trichloromethyl, fluoromethyl, difluoromethyl, trifluoromethyl, 2,2,2-trifluoroethyl, heptafluoroisopropyl, 1,1,2,2,2-pentafluoroethyl, etc.

Cycloalkyl: substituted or unsubstituted cyclic alkyl, such as cyclopropyl, cyclopentyl, or cyclohexyl; and the substituent can be, for example, methyl, halogen, cyano, etc.

Alkoxy alkyl: alkyl-O-alkyl-, for example, $CH_3O\,CH_2$—, $CH_3CH_2OCH_2$—, $CH_3CH_2CH_2OCH_2$—, $(CH_3)_2CHOCH_2$—, $CH_3CH_2CH_2CH_2OCH_2$—, $(CH_3)_3COCH_2$—, $CH_3O\,CH_2CH_2$—, $CH_3CH_2O\,CH_2CH_2$—, $CH_3CH_2CH_2O\,CH_2CH_2$—, or $CH_3CH_2CH_2CH_2O\,CH_2CH_2$—, etc.

Animal parasite control agent: refers to an active compound that can effectively reduce the incidence of various parasites in animals infected by the parasites. Control: means that active compounds can effectively kill parasites and inhibit their growth or reproduction.

Insecticide: a substance that has insecticidal efficacy on pests.

Acaricide: an agent used to control phytophagous mites.

SYNTHESIS EXAMPLES

According to the above-mentioned synthetic route, the compounds shown in Formula I of the present invention can be prepared by using different raw materials, respectively, regarding which further detailed description is as follows.

Example 1: Preparation of Compound 109

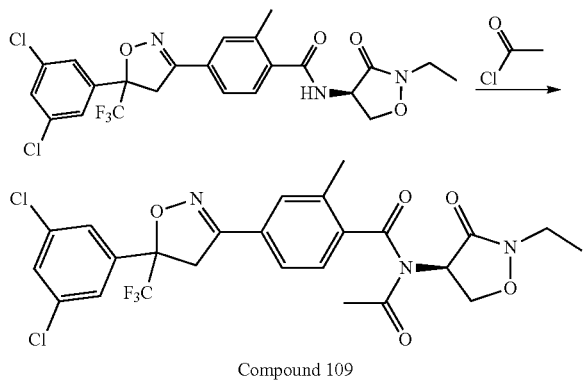

Compound 109

0.30 g (0.57 mmol) of 4-(5-(3,5-dichlorophenyl)-5-(trifluoromethyl)-4,5-dihydroisoxazole-3-yl)—N—((R)-2-ethyl-3-oxooxazolidin-4-yl)-2-methylbenzamide, 20 mL of toluene, 0.11 g (1.09 mmol) of triethylamine, and finally 66.35 mg (0.85 mmol) of acetyl chloride were added to a reaction bottle, followed by heating to reflux for reaction. After the reaction was complete, as detected by TLC, water was added to the reaction solution, which was then extracted with ethyl acetate, and the organic phase was dried over anhydrous magnesium sulfate, then filtered, concentrated, and purified by column chromatography to obtain 0.13 g of oily matter.

The NMR and MS data of Compound 109 were as follows:

$^1$H NMR (600 MHz, DMSO-d6) δ 7.83 (t, 1H), 7.71 (s, 1H), 7.67 (dt, 1H), 7.64 (d, 2H), 7.55 (d, 1H), 5.21 (t, 1H), 4.52-4.29 (m, 4H), 3.56-3.40 (m, 2H), 2.40 (s, 3H), 2.15 (s, 3H), 1.13 (t, 3H).

ESI-MS, m/Z: 594.23 [M+Na]+.

Example 2: Preparation of Compound 112

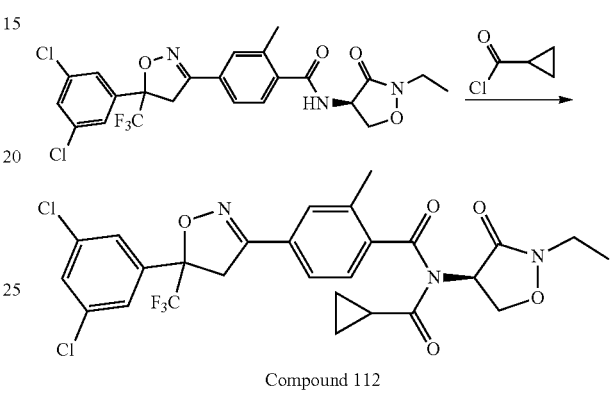

Compound 112

0.50 g (0.95 mmol) of 4-(5-(3,5-dichlorophenyl)-5-(trifluoromethyl)-4,5-dihydroisoxazol-3-yl)—N—((R)-2-ethyl-3-oxooxazolidin-4-yl)-2-methylbenzamide, 25 mL of toluene, 0.19 g (1.88 mmol) of triethylamine, and finally 0.15 g (1.44 mmol) of cyclopropanecarbonyl chloride were added to a reaction bottle, followed by heating to reflux for reaction. After the reaction was complete, as detected by TLC, water was added to the reaction solution, which was then extracted with ethyl acetate, and the organic phase was dried over anhydrous magnesium sulfate, then filtered, concentrated, and purified by column chromatography to obtain 0.29 g of yellow solid.

The NMR and MS data of Compound 112 were as follows:

$^1$H NMR (600 MHz, Chloroform-d) δ 7.63 (d, 1H), 7.60 (s, 1H), 7.56-7.49 (m, 3H), 7.44 (t, 1H), 5.56 (t, 1H), 4.56-4.42 (m, 2H), 4.08 (d, 1H), 3.75-3.56 (m, 3H), 2.52 (s, 3H), 1.40-1.15 (m, 4H), 1.11-0.94 (m, 2H), 0.60 (br s, 2H). ESI-MS, m/Z: 530.2 [M+H]+.

Example 3: Preparation of Compound 113

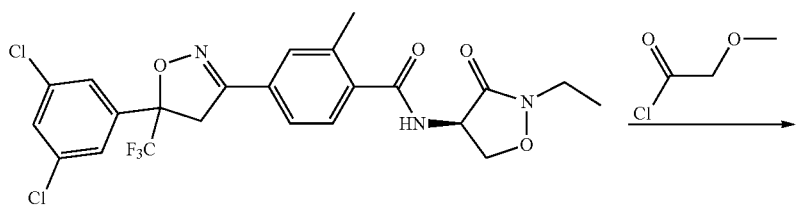

-continued

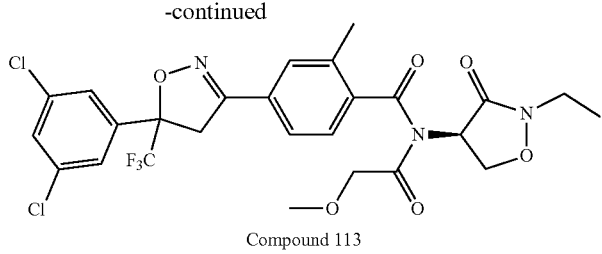

Compound 113

1.00 g (1.89 mmol) of 4-(5-(3,5-dichlorophenyl)-5-(trifluoromethyl)-4,5-dihydroisoxazol-3-yl)—N—((R)-2-ethyl-3-oxooxazolidin-4-yl)-2-methylbenzamide, 30 mL of toluene, 0.38 g (3.76 mmol) of triethylamine, and finally 0.31 g (2.87 mmol) of methoxyacetyl chloride were added to a reaction bottle, followed by heating to reflux for reaction. After the reaction was complete, as detected by TLC, water was added to the reaction solution, which was then extracted with ethyl acetate, and the organic phase was dried over anhydrous magnesium sulfate, then filtered, concentrated, and purified by column chromatography to obtain 0.53 g of oily matter.

The NMR and MS data of Compound 113 were as follows:

$^1$H NMR (600 MHz, DMSO-d6) δ 7.82 (t, 1H), 7.72 (t, 1H), 7.68-7.65 (m, 1H), 7.63 (d, 2H), 7.57 (dd, 1H), 5.08 (t, 1H), 4.49-4.28 (m, 4H), 4.15 (s, 2H), 3.57-3.36 (m, 2H), 3.22 (s, 3H), 2.39 (s, 3H), 1.12 (t, 3H). ESI-MS, m/Z: 624.25 [M+Na]+.

Example 4: Preparation of Compound 114

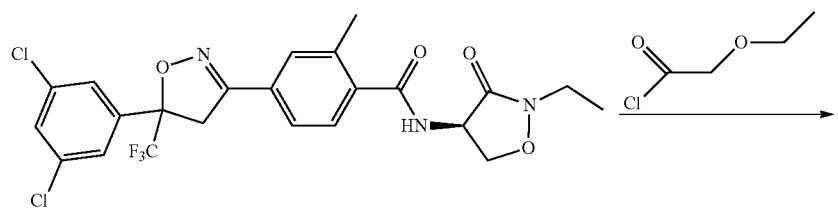

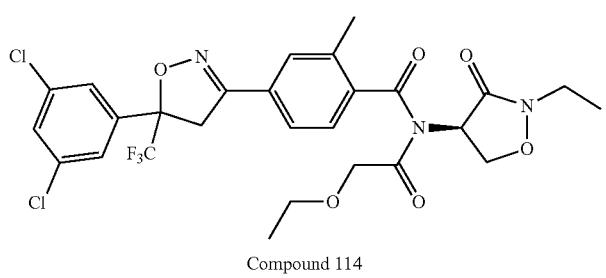

Compound 114

Compound 114 (oily matter) was prepared according to the synthesis method of Example 3.

The NMR and MS data of Compound 114 were as follows:

$^1$H NMR (600 MHz, DMSO-d6) δ 7.83 (t, 1H), 7.72 (t, 1H), 7.69-7.66 (m, 1H), 7.64 (d, 2H), 7.57 (dd, 1H), 5.08 (t, 1H), 4.48-4.30 (m, 4H), 4.20 (s, 2H), 3.54-3.39 (m, 4H), 2.40 (s, 3H), 1.13 (t, 3H), 1.09 (t, 3H). ESI-MS, m/Z: 638.37 [M+Na]+.

Example 5: Preparation of Compound 120

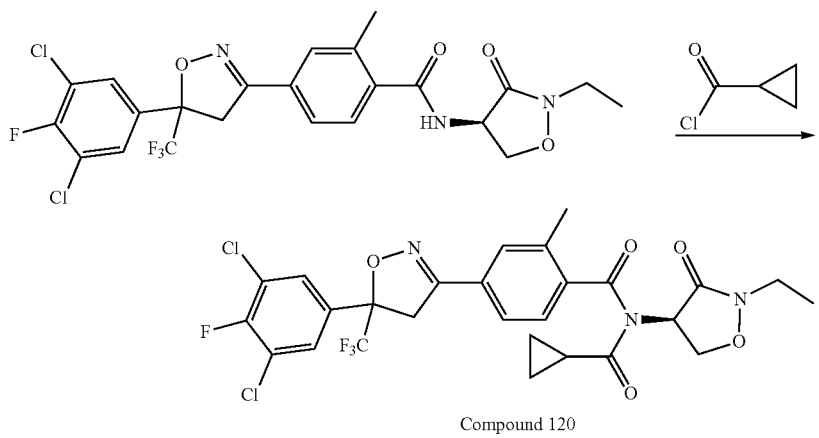

Compound 120

Compound 120 (yellow solid) was prepared according to the synthesis method of Example 2.

The NMR and MS data of Compound 120 were as follows:

$^1$H NMR (600 MHz, DMSO-d6) δ 7.82 (d, 2H), 7.69 (s, 1H), 7.66 (d, 1H), 7.56 (d, 1H), 5.54 (td, 1H), 4.58 (t, 1H), 4.46-4.30 (m, 3H), 3.57-3.44 (m, 2H), 2.43 (s, 3H), 1.42-1.35 (m, 1H), 1.15 (t, 3H), 0.87-0.78 (m, 2H), 0.77-0.58 (m, 2H). ESI-MS, m/Z: 616.30 [M+H]+.

Example 6: Preparation of Compound 121

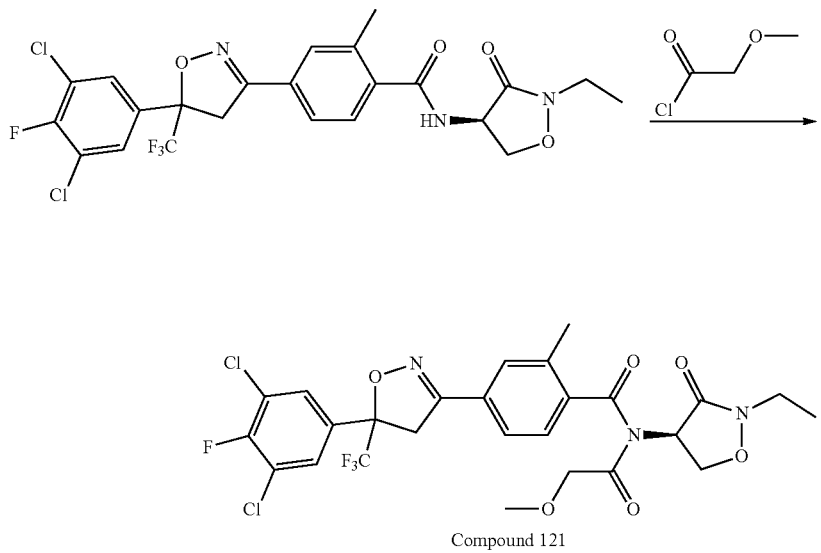

Compound 121

Compound 121 (oily matter) was prepared according to the synthesis method of Example 3.

The NMR and MS data of Compound 121 were as follows:

$^1$H NMR (600 MHz, DMSO-d6) δ 7.81 (d, 2H), 7.71 (t, 1H), 7.68-7.64 (m, 1H), 7.57 (dd, 1H), 5.08 (t, 1H), 4.48-4.29 (m, 4H), 4.15 (s, 2H), 3.53-3.40 (m, 2H), 3.22 (s, 3H), 2.39 (s, 3H), 1.13 (t, 3H). ESI-MS, m/Z: 642.13 [M+Na]+.

Example 7: Preparation of Compound 122

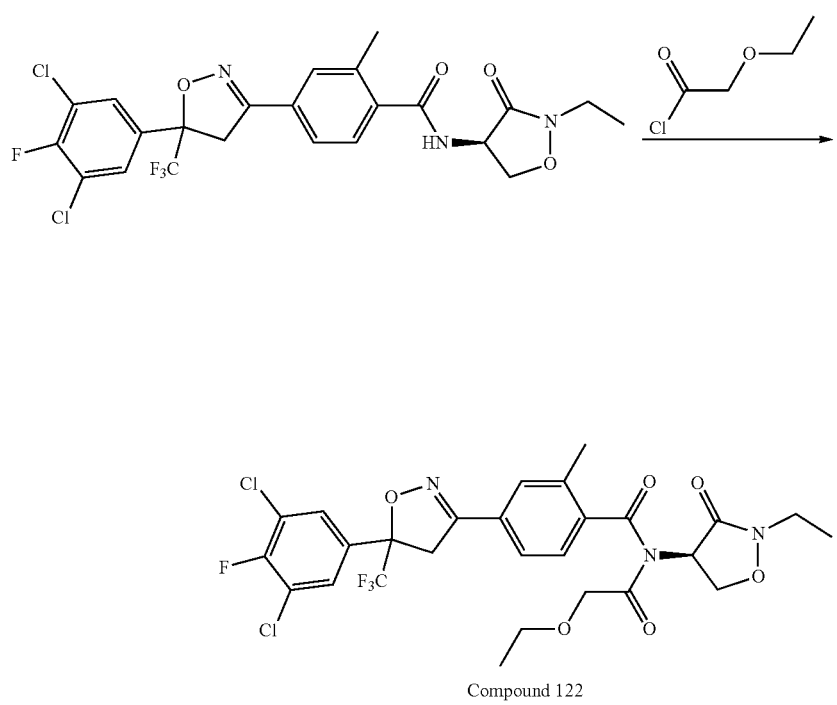

Compound 122

Compound 122 (oily matter) was prepared according to the synthesis method of Example 3.

The NMR and MS data of Compound 122 were as follows:

$^1$H NMR (600 MHz, DMSO-d6) δ 7.82 (d, 2H), 7.73-7.64 (m, 2H), 7.58 (dd, 1H), 5.08 (t, 1H), 4.49-4.31 (m, 4H), 4.20 (s, 2H), 3.55-3.40 (m, 4H), 2.40 (s, 3H), 1.13 (t, 3H), 1.09 (t, 3H).

ESI-MS, m/Z: 656.34 [M+Na]+.

Other compounds as shown in Formula I of the present invention can be prepared according to the above examples.

Determination of Biological Activity

Example 8: Determination of Biological Activities Against *Leucania separata*, *Plutella xylostella*, and *Chilo suppressalis*

The compounds of the invention were determined for the insecticidal activities against several insects. The determination method was as follows:

The compound to be determined was dissolved in a mixed solvent of acetone/methanol (1:1), followed by dilution with water containing 0.1% (wt) Tween 80 to a desired concentration.

The activities of the respective compounds against *Leucania separata*, *Plutella xylostella*, and *Chilo suppressalis* were determined by Airbrush spraying method.

(1) Determination of the Insecticidal Activity Against *Leucania Separata*

The determination method was as follows: Corn leaves were cut into 2 cm long segments; the pressure of Airbrush spraying was 10 psi (about 0.7 kg/cm$^2$); both sides of each leaf segment were sprayed with 0.5 mL of the compound solution to be tested. After drying in the shade, ten 3$^{rd}$ instar larvae were inoculated for each treatment, and each treatment was replicated 3 times. After treatment, they were cultured in an observation room at a temperature of 25° C. and a relative humidity of 60-70%, and the number of surviving insects was examined and the mortality was calculated three days after administration.

Some test results against *Leucania separata* were shown in Table 5:

TABLE 5

Insecticidal test results of the compounds of the invention against *Leucania separata*

| Compound No. | Formula | Mortality (%, 3 days after administration) | | | |
|---|---|---|---|---|---|
| | | 10 mg/L | 5 mg/L | 2.5 mg/L | 1.25 mg/L |
| 109 | | 100 | 83.33 | 63.33 | 26.67 |
| 112 | | 100 | 100 | 96.67 | 80 |
| 113 | | 100 | 100 | 100 | 100 |
| 114 | | 100 | 100 | 100 | 100 |
| 120 | | 100 | 100 | 100 | 100 |
| 121 | | 100 | 100 | 100 | 100 |

TABLE 5-continued

Insecticidal test results of the compounds of the invention against *Leucania separata*

| Compound No. | Formula | Mortality (%, 3 days after administration) | | | |
|---|---|---|---|---|---|
| | | 10 mg/L | 5 mg/L | 2.5 mg/L | 1.25 mg/L |
| 122 | (structure) | 100 | 100 | 100 | 100 |
| Comparative compound | (structure) | 73.33 | 13.33 | 0 | 0 |

In the example of the present invention, compounds with better insecticidal, acaricidal, and parasiticidal efficacy were obtained by selecting the groups $R_1$, $R_2$, and $R_3$ in the compound of formula I. As seen from the above table, when methoxy was selected as $R_3$ (i.e., the comparative compound in the above table, which was prepared according to the preparation method of the invention), its activity against *Leucania separataw* was far less than that of the compound in the example of the present invention.

(2) Determination of the Insecticidal Activity Against *Plutella xylostella*

The determination method was as follows: Cabbage leaves were made into leaf discs with a diameter of 2 cm by using a hole puncher; the pressure of Airbrush spraying was 10 psi (about 0.7 kg/cm$^2$); both sides of each leaf disc were sprayed with 0.5 mL of the compound solution to be tested. After drying in the shade, ten $3^{rd}$ instar larvae were inoculated for each treatment, and each treatment was replicated 3 times. After treatment, they were cultured in an observation room at a temperature of 25° C. and a relative humidity of 60-70%, and the number of surviving insects was examined and the mortality was calculated three days after administration.

Some test results against *Plutella xylostella* were shown in Table 6:

TABLE 6

Insecticidal test results of the compounds of the invention against *Plutella xylostella*

| Compound No. | Formula | Mortality (%, 3 days after administration) | | |
|---|---|---|---|---|
| | | 10 mg/L | 5 mg/L | 2.5 mg/L |
| 109 | (structure) | 100 | 70 | — |
| 112 | (structure) | 100 | 70 | — |

TABLE 6-continued
Insecticidal test results of the compounds of the invention against *Plutella xylostella*
| Compound No. | Formula | Mortality (%, 3 days after administration) | | |
|---|---|---|---|---|
| | | 10 mg/L | 5 mg/L | 2.5 mg/L |
| 113 | 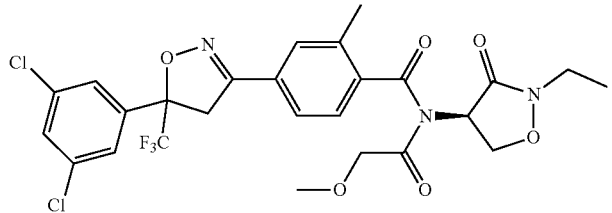 [SMILES: CCN1OC[C@@H](N(C(=O)COC)C(=O)c2ccc(C3=NOC(c4cc(Cl)cc(Cl)c4)(C(F)(F)F)C3)cc2C)C1=O] | 100 | 90 | 66.67 |
| 114 | 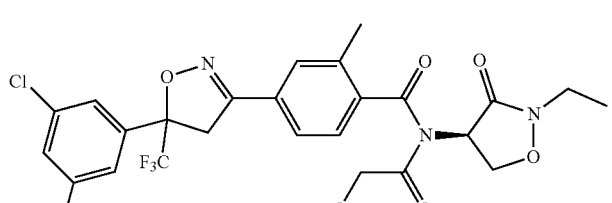 | 100 | 86.67 | 60 |
| 120 | 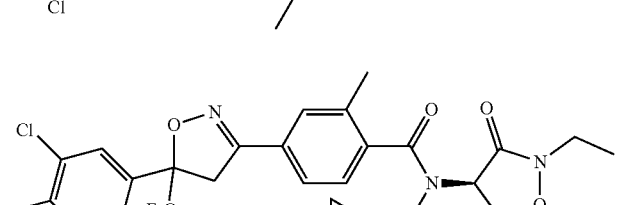 | 100 | 100 | 83.33 |
| 121 | 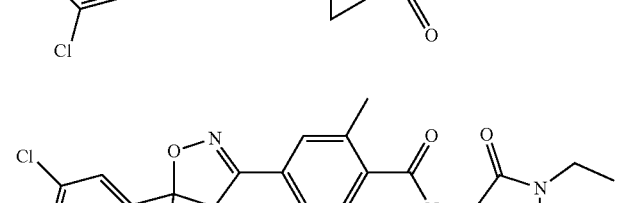 | 100 | 100 | 86.67 |
| 122 | 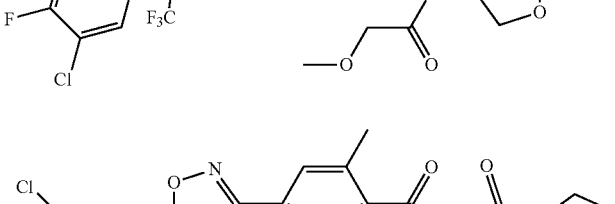 | 100 | 100 | 70 |
| Comparative compound | 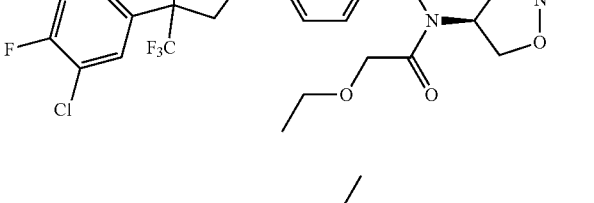 | 76.67 | 30 | 0 |

In the example of the present invention, compounds with better insecticidal, acaricidal, and parasiticidal efficacy were obtained by selecting the groups $R_1$, $R_2$, and $R_3$ in the compound of formula I. As seen from the above table, when methoxy was selected as $R_3$ (i.e., the comparative compound in the above table, which was prepared according to the preparation method of the invention), its activity against *Plutella xylostella* was far less than that of the compound in the example of the present invention.

(3) Determination of the Insecticidal Activity Against *Chilo suppressalis*

The determination method was as follows: 1) Preparation of rice seedlings: rice plants were cultivated in a plastic cup with a diameter of 4.5 cm and a height of 4 cm in a thermostatic chamber (temperature 26-28° C., relative humidity 60-80%, illumination 16 hL: 8 hD), and when the rice plants were developed to have 4-5 leaves, strong seedlings with identical growth vigour were selected for chemical treatment, and each treatment was replicated 3 times. 2) Preparation of insects to be tested: *Chilo suppressalis*, 3rd instar larvae, continuous lab rearing. 3) Inoculation of insects by spraying rice plant stems: The whole rice seedlings were sprayed evenly by using the spraying method, with 15 mL of the compound solution for each treatment. Firstly, the blank control was treated, and then the above procedure was replicated according to the order of test concentration from low to high. After rice seedlings were spray-treated, they were placed in the shade to dry, and the stems about 5 cm from the stem bases were cut off to feed the insects to be tested. Glass culture dishes with a diameter of 90 mm were prepared; each dish was padded with a filter paper at the bottom and added with water to keep moisture; about 5 rice stems were put into each dish and inoculated with 10 larvae, and each culture dish was then sealed with a non-woven and cultured in a thermostatic chamber. The number of residual live insects was examined 3 days after administration.

Some test results against *Chilo suppressalis* were shown in Table 7:

TABLE 7

Insecticidal test results of the compounds of the invention against *Chilo suppressalis*

| Compound No. | Formula | Mortality (%, 3 days after administration) | | |
|---|---|---|---|---|
| | | 10 mg/L | 2.5 mg/L | 0.625 mg/L |
| 109 | 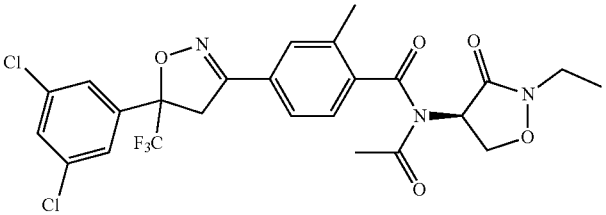 [SMILES: CCN1OC[C@@H](N(C(C)=O)C(=O)c2ccc(C3=NOC(c4cc(Cl)cc(Cl)c4)(C(F)(F)F)C3)cc2C)C1=O] | 100 | 100 | 80 |
| 112 | 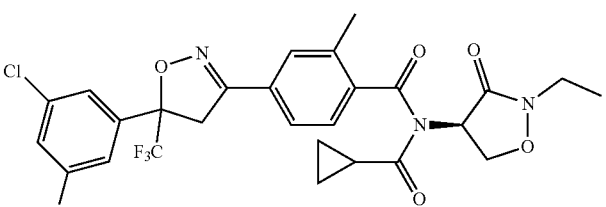 | 100 | 100 | 96.67 |
| 113 | 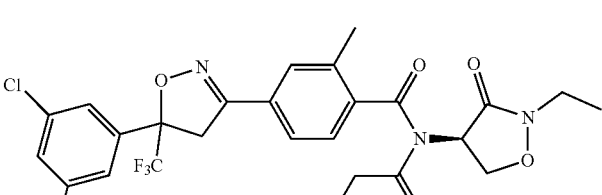 | 100 | 100 | 86.67 |
| 114 | 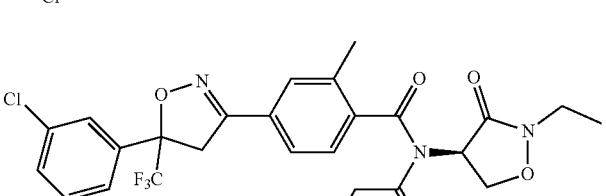 | 100 | 100 | 83.33 |

TABLE 7-continued

Insecticidal test results of the compounds of the invention against *Chilo suppressalis*

| Compound No. | Formula | Mortality (%, 3 days after administration) | | |
|---|---|---|---|---|
| | | 10 mg/L | 2.5 mg/L | 0.625 mg/L |
| 120 | | 100 | 100 | 96.67 |
| 121 | | 100 | 100 | 90 |
| 122 | | 100 | 100 | 93.33 |
| Comparative compound | | 16.67 | 0 | 0 |

In the example of the present invention, compounds with better insecticidal, acaricidal, and parasiticidal efficacy were obtained by selecting the groups $R_1$, $R_2$, and $R_3$ in the compound of formula I. As seen from the above table, when methoxy was selected as $R_3$ (i.e., the comparative compound in the above table, which was prepared according to the preparation method of the invention), its activity against *Chilo suppressalis* was far less than that of the compound in the example of the present invention.

Example 9: Determination of Biological Activity Against *Tetranychus cinnabarinus*

The compounds of the invention were determined for the acaricidal activity in greenhouse. The determination method was as follows:

The compound to be determined was dissolved in acetone or dimethyl sulfoxide according to its solubility, and 0.1% Tween 80 solution was used to formulate 50 mL of the solution to be tested at a desired concentration, and the content of acetone or dimethyl sulfoxide in the solution did not exceed 10%.

A bean seedling with two true leaves was taken for inoculating 30-40 adult mites of *Tetranychus cinnabarinus*. After examining the cardinal number, the whole seedling was treated by spraying with a hand-held sprayer, each treatment being replicated 3 times, and then placed in a standard observation room. The number of surviving mites was examined after 72 hours, and the mortality was calculated.

Some test results against *Tetranychus cinnabarinus* were shown in Table 8:

TABLE 8

The acaricidal test results of the compounds of the invention against *Tetranychus cinnabarinus*

| Compound No. | Formula | Mortality (%, 3 days after treatment) | | | |
| --- | --- | --- | --- | --- | --- |
| | | 5 mg/L | 2.5 mg/L | 1.25 mg/L | 0.625 mg/L |
| 109 | | 100 | 100 | 70 | 16.7 |
| 112 | | 100 | 100 | 100 | 96.7 |
| 113 | | 100 | 100 | 100 | 100 |
| 114 | | 100 | 100 | 100 | 100 |
| 120 | | 100 | 100 | 100 | 100 |
| 121 | | 100 | 100 | 100 | 100 |

TABLE 8-continued

The acaricidal test results of the compounds of the invention against *Tetranychus cinnabarinus*

| Compound No. | Formula | Mortality (%, 3 days after treatment) | | | |
|---|---|---|---|---|---|
| | | 5 mg/L | 2.5 mg/L | 1.25 mg/L | 0.625 mg/L |
| 122 | | 100 | 100 | 100 | 100 |
| Comparative compound | | 100 | 73.3 | 20 | — |

In the example of the present invention, compounds with better insecticidal, acaricidal, and parasiticidal efficacy were obtained by selecting the groups $R_1$, $R_2$, and $R_3$ in the compound of formula I. As seen from the above table, when methoxy was selected as $R_3$ (i.e., the comparative compound in the above table, which was prepared according to the preparation method of the invention), its activity against *Tetranychus cinnabarinus* was far less than that of the compound in the example of the present invention.

Example 10: Insecticidal Test Against Cat Fleas 4 mg of then mon to be tested was dissolved into 40 mL of acetone to obtain an acetone solution with a concentration of 100 ppm. 400 µL of the resultant solution was applied onto the bottom and side of a culture dish with an inner diameter of 5.3 cm, followed by standing until acetone was volatilized. A film of the compound of the invention was made on the inner wall of the culture dish. The inner wall of the used culture dish was 40 cm² and was treated with a dose of 1 µg/cm²; and ten adult cat fleas (male and female mixed) were put into the culture dish, which then was covered and stored in a thermostatic chamber at 25° C. The number of dead insects was examined after 72 hours, and the mortality was calculated. The test was replicated 3 times. Test results: Compounds 109, 112, 113, 114, 120, 121, 122 showed more than 70% mortality of insects.

Example 11: Insecticidal Test Against American Dog Ticks 4 mg of the compound to be tested was dissolved into 40 mL of acetone to obtain an acetone solution with a concentration of 100 ppm. 400 µL of the resultant solution was applied onto the bottom and side of each of two culture dishes with an inner diameter of 5.3 cm, followed by standing until acetone was volatilized. A film of the compound of the invention was made on the inner wall of each culture dish. The inner wall of the used culture dish was 40 cm² and was treated with a dose of 1 µg/cm². Ten level 1 nymph (male and female mixed) of American dog ticks were put into each of the two culture dishes, and then the two culture dishes were combined and sealed at the joint with a tape to prevent escape, and then stored in a thermostatic chamber at 25° C. The number of dead insects was examined after 24 hours, and the mortality was calculated. The test was replicated 3 times. Test results: Compounds 109, 112, 113, 114, 120, 121, 122 showed more than 70% mortality of insects.

INDUSTRIAL APPLICABILITY

The invention has disclosed an isoxazoline compound, the preparation method therefor, and the application thereof. The isoxazoline compound has unexpectedly excellent insecticidal and acaricidal efficacy, and also exhibits appropriate control efficacy on poisonous pests without phytotoxicity to cultivated crops and plants. In addition, the compounds of the present invention may be used to control, disinfect, and kill various pests, such as harmful piercing-sucking insects, chewing insects, and other plant parasitic pests, stored grain pests, sanitary pests, and the like.

The invention claimed is:
1. An isoxazoline compound as shown in Formula I:

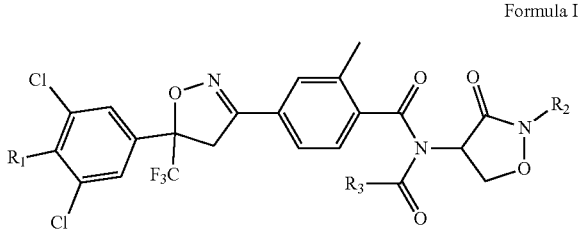

Formula I

In Formula I:
$R_1$ is selected from hydrogen, chlorine, or fluorine;
$R_2$ is selected from ethyl or 2,2,2-trifluoroethyl;
$R_3$ is selected from $C_1$-$C_6$ alkyl, $C_1$-$C_6$ haloalkyl, $C_3$-$C_8$ cycloalkyl, or $C_1$-$C_6$ alkoxy $C_1$-$C_6$ alkyl;
or a stereoisomer of the compound of Formula I;
or a salt of the compound of Formula I;
or a salt of a stereoisomer of the compound of Formula I.

2. The isoxazoline compound according to claim 1, wherein in Formula I:
$R_1$ is selected from hydrogen, chlorine, or fluorine;
$R_2$ is selected from ethyl or 2,2,2-trifluoroethyl;
$R_3$ is selected from $C_1$-$C_4$ alkyl, $C_1$-$C_4$ haloalkyl, $C_3$-$C_4$ cycloalkyl, or $C_1$-$C_4$ alkoxy $C_1$-$C_3$ alkyl.

3. The isoxazoline compound according to claim 2, wherein in Formula I:
$R_1$ is selected from hydrogen, chlorine, or fluorine;
$R_2$ is selected from ethyl or 2,2,2-trifluoroethyl;
$R_3$ is selected from $C_1$-$C_4$ alkyl, cyclopropyl, or $C_1$-$C_4$ alkoxy $C_1$-$C_2$ alkyl.

4. The isoxazoline compound according to claim 1, wherein the salt of the compound of Formula I includes: a salt formed by the reaction of the compound of Formula I with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid;
and/or, the salt of the stereoisomer of the compound of Formula I includes a salt formed by the reaction of the stereoisomer of the compound of Formula I with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid.

5. The isoxazoline compound according to claim 1, wherein the isoxazoline compound is selected from the compounds in Table 1, which have the structure of Formula I with $R_1$, $R_2$, and $R_3$ being those listed in Table 1:

TABLE 1

| Compound No. | $R_1$ | $R_2$ | $R_3$ |
|---|---|---|---|
| 1 | H | ethyl | methyl |
| 2 | H | ethyl | ethyl |
| 3 | H | ethyl | n-propyl |
| 4 | H | ethyl | isopropyl |
| 5 | H | ethyl | n-butyl |
| 6 | H | ethyl | isobutyl |
| 7 | H | ethyl | tert-butyl |
| 8 | H | ethyl | cyclopropyl |
| 9 | H | ethyl | $CH_3OCH_2$— |
| 10 | H | ethyl | $CH_3CH_2OCH_2$— |
| 11 | H | ethyl | $CH_3CH_2CH_2OCH_2$— |
| 12 | H | ethyl | $(CH_3)_2CHOCH_2$— |
| 13 | H | ethyl | $CH_3CH_2CH_2CH_2OCH_2$— |
| 14 | H | ethyl | $(CH_3)_3COCH_2$— |
| 15 | H | ethyl | $CH_3OCH_2$— |
| 16 | H | ethyl | $CH_3CH_2OCH_2CH_2$— |
| 17 | H | ethyl | $CH_3CH_2CH_2OCH_2CH_2$— |
| 18 | H | ethyl | $CH_3CH_2CH_2CH_2OCH_2CH_2$— |
| 19 | F | ethyl | methyl |
| 20 | F | ethyl | ethyl |
| 21 | F | ethyl | n-propyl |
| 22 | F | ethyl | isopropyl |
| 23 | F | ethyl | n-butyl |
| 24 | F | ethyl | i sobutyl |
| 25 | F | ethyl | tert-butyl |
| 26 | F | ethyl | cyclopropyl |
| 27 | F | ethyl | $CH_3OCH_2$— |
| 28 | F | ethyl | $CH_3CH_2OCH_2$— |
| 29 | F | ethyl | $CH_3CH_2CH_2OCH_2$— |
| 30 | F | ethyl | $(CH_3)_2CHOCH_2$— |
| 31 | F | ethyl | $CH_3CH_2CH_2CH_2OCH_2$— |
| 32 | F | ethyl | $(CH_3)_3COCH_2$— |
| 33 | F | ethyl | $CH_3OCH_2CH_2$— |
| 34 | F | ethyl | $CH_3CH_2OCH_2CH_2$— |
| 35 | F | ethyl | $CH_3CH_2CH_2OCH_2CH_2$— |
| 36 | F | ethyl | $CH_3CH_2CH_2CH_2OCH_2CH_2$— |
| 37 | H | 2,2,2-trifluoroethyl | methyl |
| 38 | H | 2,2,2-trifluoroethyl | ethyl |
| 39 | H | 2,2,2-trifluoroethyl | n-propyl |
| 40 | H | 2,2,2-trifluoroethyl | isopropyl |
| 41 | H | 2,2,2-trifluoroethyl | n-butyl |
| 42 | H | 2,2,2-trifluoroethyl | isobutyl |
| 43 | H | 2,2,2-trifluoroethyl | tert-butyl |
| 44 | H | 2,2,2-trifluoroethyl | cyclopropyl |
| 45 | H | 2,2,2-trifluoroethyl | $CH_3OCH_2$— |
| 46 | H | 2,2,2-trifluoroethyl | $CH_3CH_2OCH_2$— |
| 47 | H | 2,2,2-trifluoroethyl | $CH_3CH_2CH_2OCH_2$— |
| 48 | H | 2,2,2-trifluoroethyl | $(CH_3)_2CHOCH_2$— |
| 49 | H | 2,2,2-trifluoroethyl | $CH_3CH_2CH_2CH_2OCH_2$— |
| 50 | H | 2,2,2-trifluoroethyl | $(CH_3)_3COCH_2$— |
| 51 | H | 2,2,2-trifluoroethyl | $CH_3OCH_2$— |
| 52 | H | 2,2,2-trifluoroethyl | $CH_3CH_2OCH_2CH_2$— |
| 53 | H | 2,2,2-trifluoroethyl | $CH_3CH_2CH_2OCH_2CH_2$— |
| 54 | H | 2,2,2-trifluoroethyl | $CH_3CH_2CH_2CH_2OCH_2CH_2$— |
| 55 | F | 2,2,2-trifluoroethyl | methyl |
| 56 | F | 2,2,2-trifluoroethyl | ethyl |
| 57 | F | 2,2,2-trifluoroethyl | n-propyl |
| 58 | F | 2,2,2-trifluoroethyl | isopropyl |
| 59 | F | 2,2,2-trifluoroethyl | n-butyl |
| 60 | F | 2,2,2-trifluoroethyl | isobutyl |
| 61 | F | 2,2,2-trifluoroethyl | tert-butyl |
| 62 | F | 2,2,2-trifluoroethyl | cyclopropyl |
| 63 | F | 2,2,2-trifluoroethyl | $CH_3OCH_2$— |
| 64 | F | 2,2,2-trifluoroethyl | $CH_3CH_2OCH_2$— |
| 65 | F | 2,2,2-trifluoroethyl | $CH_3CH_2CH_2OCH_2$— |
| 66 | F | 2,2,2-trifluoroethyl | $(CH_3)_2CHOCH_2$— |
| 67 | F | 2,2,2-trifluoroethyl | $CH_3CH_2CH_2CH_2OCH_2$— |
| 68 | F | 2,2,2-trifluoroethyl | $(CH_3)_3COCH_2$— |
| 69 | F | 2,2,2-trifluoroethyl | $CH_3OCH_2$— |
| 70 | F | 2,2,2-trifluoroethyl | $CH_3CH_2OCH_2$— |
| 71 | F | 2,2,2-trifluoroethyl | $CH_3CH_2CH_2OCH_2CH_2$— |
| 72 | F | 2,2,2-trifluoroethyl | $CH_3CH_2CH_2CH_2OCH_2CH_2$— |
| 73 | Cl | ethyl | methyl |
| 74 | Cl | ethyl | ethyl |
| 75 | Cl | ethyl | n-propyl |
| 76 | Cl | ethyl | isopropyl |
| 77 | Cl | ethyl | n-butyl |
| 78 | Cl | ethyl | isobutyl |
| 79 | Cl | ethyl | tert-butyl |
| 80 | Cl | ethyl | cyclopropyl |
| 81 | Cl | ethyl | $CH_3OCH_2$— |
| 82 | Cl | ethyl | $CH_3CH_2OCH_2$— |
| 83 | Cl | ethyl | $CH_3CH_2CH_2OCH_2$— |
| 84 | Cl | ethyl | $(CH_3)_2CHOCH_2$— |
| 85 | Cl | ethyl | $CH_3CH_2CH_2CH_2OCH_2$— |
| 86 | Cl | ethyl | $(CH_3)_3COCH_2$— |
| 87 | Cl | ethyl | $CH_3OCH_2$— |
| 88 | Cl | ethyl | $CH_3CH_2OCH_2CH_2$— |
| 89 | Cl | ethyl | $CH_3CH_2CH_2OCH_2CH_2$— |
| 90 | Cl | ethyl | $CH_3CH_2CH_2CH_2OCH_2CH_2$— |
| 91 | Cl | 2,2,2-trifluoroethyl | methyl |
| 92 | Cl | 2,2,2-trifluoroethyl | ethyl |
| 93 | Cl | 2,2,2-trifluoroethyl | n-propyl |
| 94 | Cl | 2,2,2-trifluoroethyl | isopropyl |
| 95 | Cl | 2,2,2-trifluoroethyl | n-butyl |
| 96 | Cl | 2,2,2-trifluoroethyl | isobutyl |
| 97 | Cl | 2,2,2-trifluoroethyl | tert-butyl |
| 98 | Cl | 2,2,2-trifluoroethyl | cyclopropyl |
| 99 | Cl | 2,2,2-trifluoroethyl | $CH_3OCH_2$— |
| 100 | Cl | 2,2,2-trifluoroethyl | $CH_3CH_2OCH_2$— |

TABLE 1-continued

| Compound No. | R₁ | R₂ | R₃ |
|---|---|---|---|
| 101 | Cl | 2,2,2-trifluoroethyl | CH₃CH₂CH₂OCH₂— |
| 102 | Cl | 2,2,2-trifluoroethyl | (CH₃)₂CHOCH₂— |
| 103 | Cl | 2,2,2-trifluoroethyl | CH₃CH₂CH₂CH₂OCH₂— |
| 104 | Cl | 2,2,2-trifluoroethyl | (CH₃)₃COCH₂— |
| 105 | Cl | 2,2,2-trifluoroethyl | CH₃OCH₂CH₂— |
| 106 | Cl | 2,2,2-trifluoroethyl | CH₃CH₂OCH₂CH₂— |
| 107 | Cl | 2,2,2-trifluoroethyl | CH₃CH₂CH₂OCH₂CH₂— |
| 108 | Cl | 2,2,2-trifluoroethyl | CH₃CH₂CH₂CH₂OCH₂CH₂— | or a stereoisomer of any one of the compounds from Table 1;

or a salt formed by the reaction of any one of the compounds from Table 1 with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid;

or a salt formed by the reaction of a stereoisomer of any one of the compounds from Table 1 with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid.

6. The isoxazoline compound according to claim 5, wherein the isoxazoline compound is selected from the compounds in Table 2, which have the structure of Formula I with $R_1$, $R_2$, and $R_3$ being those listed in Table 2:

TABLE 2

| Compound No. | R₁ | R₂ | R₃ |
|---|---|---|---|
| 1 | H | ethyl | methyl |
| 2 | H | ethyl | ethyl |
| 3 | H | ethyl | n-propyl |
| 4 | H | ethyl | isopropyl |
| 5 | H | ethyl | n-butyl |
| 6 | H | ethyl | i sobutyl |
| 7 | H | ethyl | tert-butyl |
| 8 | H | ethyl | cyclopropyl |
| 9 | H | ethyl | CH₃OCH₂— |
| 10 | H | ethyl | CH₃CH₂OCH₂— |
| 11 | H | ethyl | CH₃CH₂CH₂OCH₂— |
| 12 | H | ethyl | (CH₃)₂CHOCH₂— |
| 19 | F | ethyl | methyl |
| 20 | F | ethyl | ethyl |
| 21 | F | ethyl | n-propyl |
| 22 | F | ethyl | isopropyl |
| 23 | F | ethyl | n-butyl |
| 24 | F | ethyl | i sobutyl |
| 25 | F | ethyl | tert-butyl |
| 26 | F | ethyl | cyclopropyl |
| 27 | F | ethyl | CH₃OCH₂— |
| 28 | F | ethyl | CH₃CH₂OCH₂— |
| 29 | F | ethyl | CH₃CH₂CH₂OCH₂— |
| 30 | F | ethyl | (CH₃)₂CHOCH₂— |
| 37 | H | 2,2,2-trifluoroethyl | methyl |
| 38 | H | 2,2,2-trifluoroethyl | ethyl |
| 39 | H | 2,2,2-trifluoroethyl | n-propyl |
| 40 | H | 2,2,2-trifluoroethyl | isopropyl |
| 41 | H | 2,2,2-trifluoroethyl | n-butyl |
| 42 | H | 2,2,2-trifluoroethyl | i sobutyl |
| 43 | H | 2,2,2-trifluoroethyl | tert-butyl |
| 44 | H | 2,2,2-trifluoroethyl | cyclopropyl |
| 45 | H | 2,2,2-trifluoroethyl | CH₃OCH₂— |
| 46 | H | 2,2,2-trifluoroethyl | CH₃CH₂OCH₂— |
| 47 | H | 2,2,2-trifluoroethyl | CH₃CH₂CH₂OCH₂— |
| 48 | H | 2,2,2-trifluoroethyl | (CH₃)₂CHOCH₂— |
| 55 | F | 2,2,2-trifluoroethyl | methyl |
| 56 | F | 2,2,2-trifluoroethyl | ethyl |
| 57 | F | 2,2,2-trifluoroethyl | n-propyl |
| 58 | F | 2,2,2-trifluoroethyl | isopropyl |
| 59 | F | 2,2,2-trifluoroethyl | n-butyl |
| 60 | F | 2,2,2-trifluoroethyl | isobutyl |
| 61 | F | 2,2,2-trifluoroethyl | tert-butyl |
| 62 | F | 2,2,2-trifluoroethyl | cyclopropyl |
| 63 | F | 2,2,2-trifluoroethyl | CH₃OCH₂— |
| 64 | F | 2,2,2-trifluoroethyl | CH₃CH₂OCH₂— |
| 65 | F | 2,2,2-trifluoroethyl | CH₃CH₂CH₂OCH₂— |
| 66 | F | 2,2,2-trifluoroethyl | (CH₃)₂CHOCH₂— |
| 73 | Cl | ethyl | methyl |
| 74 | Cl | ethyl | ethyl |
| 75 | Cl | ethyl | n-propyl |
| 76 | Cl | ethyl | isopropyl |
| 77 | Cl | ethyl | n-butyl |
| 78 | Cl | ethyl | isobutyl |
| 79 | Cl | ethyl | tert-butyl |
| 80 | Cl | ethyl | cyclopropyl |
| 81 | Cl | ethyl | CH₃OCH₂— |
| 82 | Cl | ethyl | CH₃CH₂OCH₂— |
| 83 | Cl | ethyl | CH₃CH₂CH₂OCH₂— |
| 84 | Cl | ethyl | (CH₃)₂CHOCH₂— |
| 91 | Cl | 2,2,2-trifluoroethyl | methyl |
| 92 | Cl | 2,2,2-trifluoroethyl | ethyl |
| 93 | Cl | 2,2,2-trifluoroethyl | n-propyl |
| 94 | Cl | 2,2,2-trifluoroethyl | isopropyl |
| 95 | Cl | 2,2,2-trifluoroethyl | n-butyl |
| 96 | Cl | 2,2,2-trifluoroethyl | isobutyl |
| 97 | Cl | 2,2,2-trifluoroethyl | tert-butyl |
| 98 | Cl | 2,2,2-trifluoroethyl | cyclopropyl |
| 99 | Cl | 2,2,2-trifluoroethyl | CH₃OCH₂— |
| 100 | Cl | 2,2,2-trifluoroethyl | CH₃CH₂OCH₂— |
| 101 | Cl | 2,2,2-trifluoroethyl | CH₃CH₂CH₂OCH₂— |
| 102 | Cl | 2,2,2-trifluoroethyl | (CH₃)₂CHOCH₂— | or a stereoisomer of any one of the compounds from Table 2, or a salt formed by the reaction of any one of the compounds from Table 2 with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid, or a salt formed by the reaction of a stereoisomer of any one of the compounds from Table 2 with hydrochloric acid, hydrobromic acid, sulfuric acid, phosphoric acid, formic acid, acetic acid, propionic acid, butyric acid, valeric acid, trifluoroacetic acid, oxalic acid, malonic acid, methanesulfonic acid, 4-toluenesulfonic acid, malic acid, fumaric acid, lactic acid, maleic acid, salicylic acid, tartaric acid, or citric acid.

7. The isoxazoline compound according to claim 1, wherein the stereoisomer of the compound of Formula I is the compound as shown in Formula IA, Formula IA

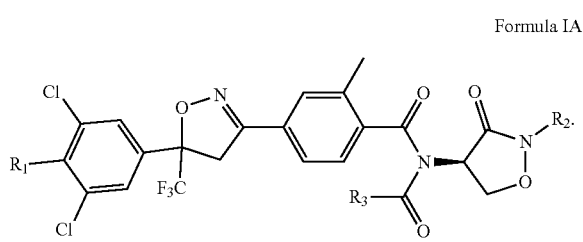

8. The isoxazoline compound according to claim 7, wherein the compound as shown in Formula IA is selected from the compounds in Table 3, which have the structure as shown in Formula IA with $R_1$, $R_2$, and $R_3$ being those listed in Table 3,

TABLE 3

| Compound No. | $R_1$ | $R_2$ | $R_3$ |
|---|---|---|---|
| 109 | H | ethyl | methyl |
| 110 | H | ethyl | ethyl |
| 111 | H | ethyl | isopropyl |
| 112 | H | ethyl | cyclopropyl |
| 113 | H | ethyl | $CH_3OCH_2$— |
| 114 | H | ethyl | $CH_3CH_2OCH_2$— |
| 115 | H | ethyl | $CH_3OCH_2CH_2$— |
| 116 | H | ethyl | $CH_3CH_2OCH_2CH_2$— |
| 117 | F | ethyl | methyl |
| 118 | F | ethyl | ethyl |
| 119 | F | ethyl | isopropyl |
| 120 | F | ethyl | cyclopropyl |
| 121 | F | ethyl | $CH_3OCH_2$— |
| 122 | F | ethyl | $CH_3CH_2OCH_2$— |
| 123 | F | ethyl | $CH_3OCH_2CH_2$— |
| 124 | F | ethyl | $CH_3CH_2OCH_2CH_2$—. |

9. The compound according to claim 8, wherein the compound as shown in Formula IA is selected from the compounds in Table 4, which have the structure as shown in Formula IA with $R_1$, $R_2$, and $R_3$ being those listed in Table 4,

TABLE 4

| Compound No. | $R_1$ | $R_2$ | $R_3$ |
|---|---|---|---|
| 109 | H | ethyl | methyl |
| 110 | H | ethyl | ethyl |
| 111 | H | ethyl | isopropyl |
| 112 | H | ethyl | cyclopropyl |
| 113 | H | ethyl | $CH_3OCH_2$— |
| 114 | H | ethyl | $CH_3CH_2OCH_2$— |
| 117 | F | ethyl | methyl |
| 118 | F | ethyl | ethyl |
| 119 | F | ethyl | isopropyl |
| 120 | F | ethyl | cyclopropyl |
| 121 | F | ethyl | $CH_3OCH_2$— |
| 122 | F | ethyl | $CH_3CH_2OCH_2$—. |

10. A method for preparing the isoxazoline compound according to claim 1, wherein when the isoxazoline compound is the compound of Formula I, the method comprises the following steps, in which the meanings of $R_1$, $R_2$, and $R_3$ in the reaction formula are the same as those in claim 1:

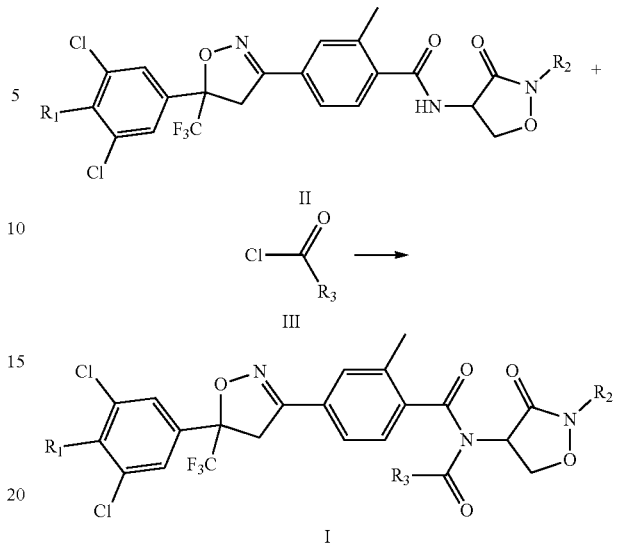

the compound of Formula II and the compound of Formula III are allowed to react in a solvent at a temperature from −10° C. to the boiling point of the solvent for 0.5-48 hours to prepare the compound of Formula I; the reaction can be carried out in the presence of alkali.

11. An insecticide formulation or acaricide formulation, wherein the insecticide formulation or acaricide formulation contains the isoxazoline compound according to claim 1 as an active ingredient, and also contains one or more adjuvants; optionally, the amount of the isoxazoline compound in the insecticide formulation or acaricide formulation is 0.1 to 99% by weight, and further optionally 0.5 to 90% by weight.

12. An insecticide composition or acaricide composition, comprising a mixture of the isoxazoline compound according to claim 1 and an additional active compound, in which the additional active compound is one or more of an insecticide, a poison bait, a disinfectant, an acaricide, a nematicide, a fungicide, a growth regulator, and an herbicide.

13. A method for controlling agricultural or forestry pests and/or mites, comprising applying an effective dose of material to the pests and/or mites to be controlled, or to their growth media, in which the material is the isoxazoline compound according to claim 1.

14. An animal parasite control agent, comprising the isoxazoline compound according to claim 1 as an active component, and one or more adjuvants; optionally, the amount of the isoxazoline compound in the animal parasite control agent is 1 to 80 wt %.

15. An animal parasite control composition, comprising a mixture of the isoxazoline compound according to claim 1 and an additional animal parasite control active compound, wherein the additional animal parasite control active compound is one or more of acaricides, insecticides, parasiticides, and antiplasmodium agents.

16. A method for controlling animal parasites, comprising the following steps: applying an effective dose of material to the animal parasites to be controlled, or to their growth media, wherein the material is the isoxazoline compound according to claim 1.

17. The method according to claim 13, wherein the pests and/or mites are selected from *Leucania separata*, *Plutella xylostella*, *Chilo suppressalis*, and *Tetranychus cinnabarinus*.

18. The method according to claim 16, wherein the animal parasites are selected from cat fleas and American dog ticks.

\* \* \* \* \*